(12) United States Patent
Paolitto et al.

(10) Patent No.: US 7,264,000 B2
(45) Date of Patent: Sep. 4, 2007

(54) SURGICAL APPARATUS AND METHOD FOR PERFORMING TRANSABDOMINAL CARDIAC SURGERY

(75) Inventors: Anthony Paolitto, St. Leonard (CA); Valerio Valentini, Montreal (CA); Raymond Cartier, Montreal (CA)

(73) Assignee: Coroneo, Inc., Montreal (CA)

( * ) Notice: Subject to any disclaimer, the term of this patent is extended or adjusted under 35 U.S.C. 154(b) by 0 days.

(21) Appl. No.: 10/243,764

(22) Filed: Sep. 16, 2002

(65) Prior Publication Data

US 2003/0010346 A1 Jan. 16, 2003

Related U.S. Application Data

(63) Continuation of application No. 09/488,557, filed on Jan. 21, 2000, now Pat. No. 6,478,028.

(30) Foreign Application Priority Data

Jan. 21, 1999 (CA) .................... 2261488

(51) Int. Cl.
*A61B 19/00* (2006.01)
(52) U.S. Cl. .................................... 128/898
(58) Field of Classification Search ............... 128/898; 600/201, 202, 203, 204, 205, 221, 235; 604/264, 604/533
See application file for complete search history.

(56) References Cited

U.S. PATENT DOCUMENTS

| | | | |
|---|---|---|---|
| 4,270,549 A | 6/1981 | Heilman | |
| 5,894,843 A | 4/1999 | Benetti et al. | |
| 5,910,124 A | 6/1999 | Rubin | |
| 6,017,304 A | 1/2000 | Vierra et al. | |
| 6,059,750 A | 5/2000 | Fogarty et al. | |
| 6,083,260 A | 7/2000 | Aboul-Hosn et al. | |

FOREIGN PATENT DOCUMENTS

| | | | |
|---|---|---|---|
| EP | 0 095 727 | * | 7/1983 |
| EP | 095 727 | * | 7/1983 |
| WO | WO96/40354 | | 12/1996 |

OTHER PUBLICATIONS

Shahian et al "The role of coronary revascularization in recipients of an implantable cardioverter-defibrillator."J Thorac Cardiovasc Surg. Oct. 1995;110(4 Pt 1):Abstract. http://www.ncbi.nlm.nih.gov/entrez/query.fcgi?cmd=Retrieve&db=PubMed&list_uids=747512.*

* cited by examiner

*Primary Examiner*—Corrine McDermott
*Assistant Examiner*—Thomas J. Sweet
(74) *Attorney, Agent, or Firm*—Wood, Herron & Evans, L.L.P.

(57) ABSTRACT

An intervention is performed on a target anatomic structure of a patient body by first altering the configuration of the diaphragm through displacement or puncturing of the latter, in order to create a passageway leading into the thoracic cavity. An implement is introduced into the thoracic cavity through the passageway. The implement is then used while extending through the passageway to alter a biological tissue of the target structure or manipulate the latter. Optionally, a separating component having a peripheral wall encompassing a component channel is introduced into the passageway for receiving the implement and separating the latter from the non-target anatomic structure.

31 Claims, 29 Drawing Sheets

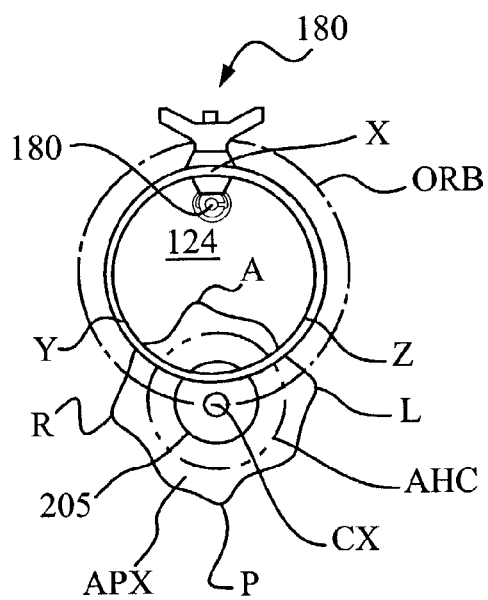
Figure 15A
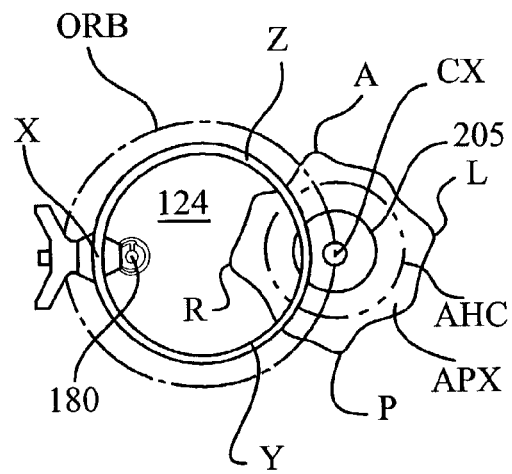
Figure 15B
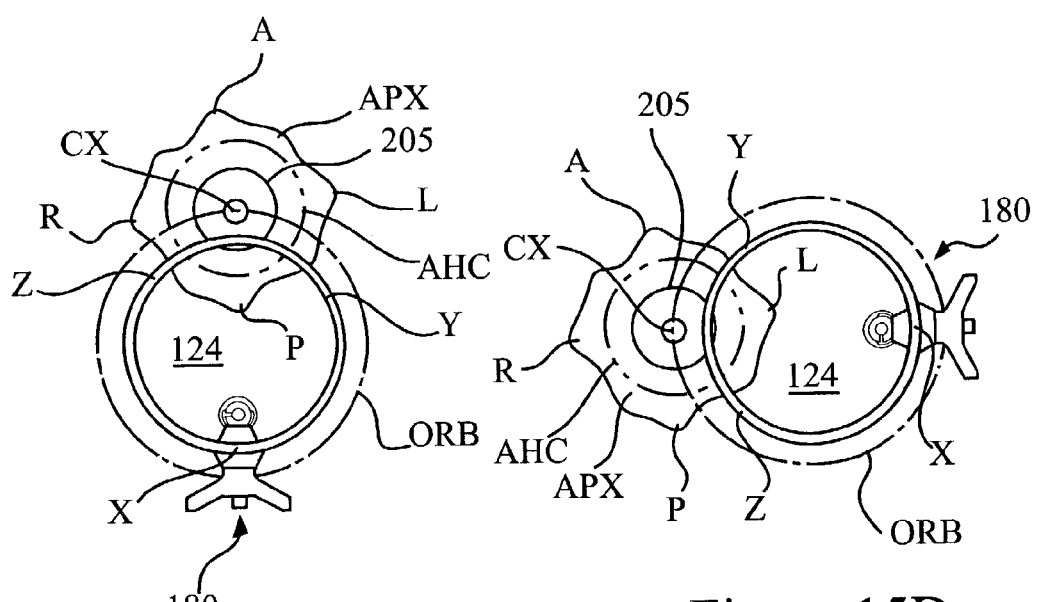
Figure 15C
Figure 15D

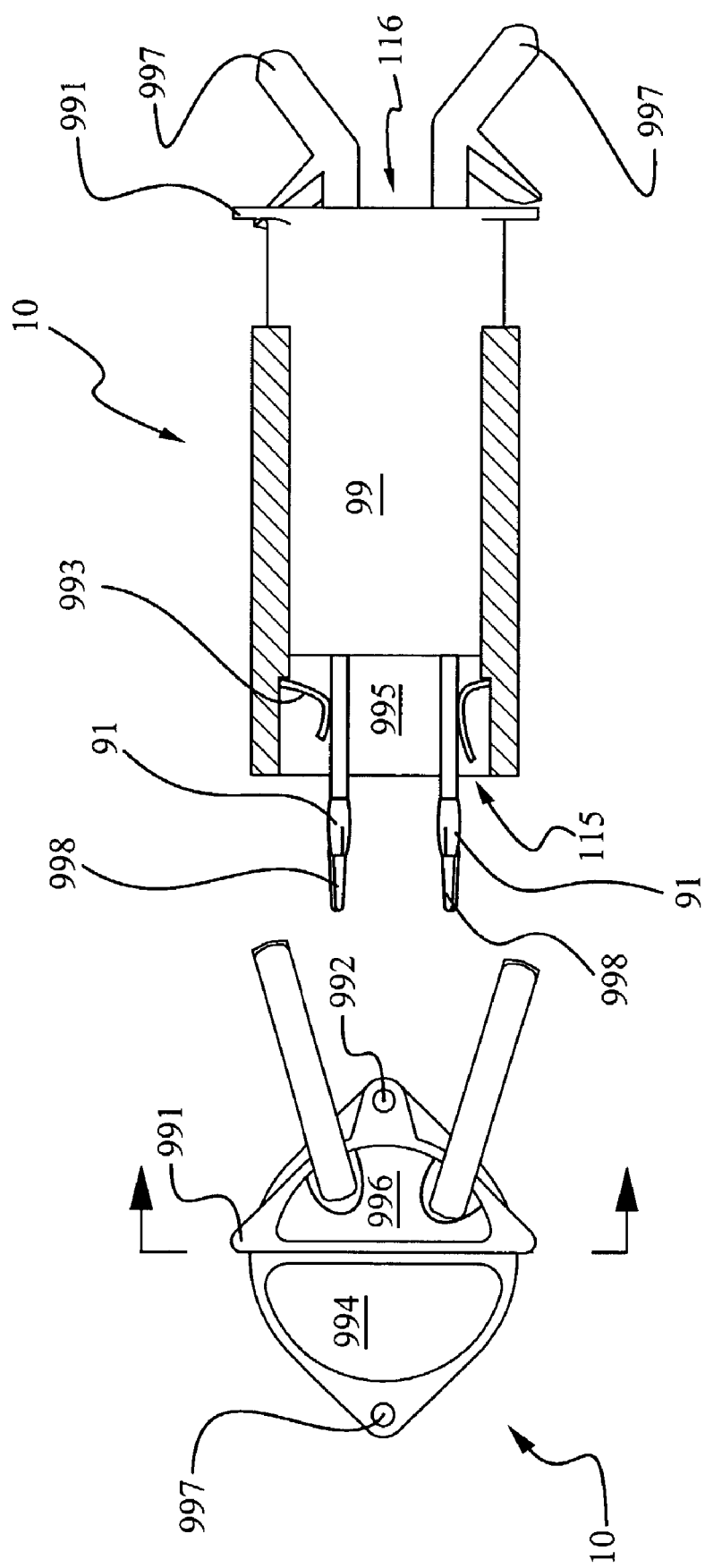

SURGICAL APPARATUS AND METHOD FOR PERFORMING TRANSABDOMINAL CARDIAC SURGERY

CROSS REFERENCE TO RELATED APPLICATION

This application is a continuation application of U.S. patent application Ser. No. 09/488,557, now U.S. Pat. No. 6,478,028, filed on Jan. 21, 2000.

FIELD OF THE INVENTION

The present invention relates generally to a surgical apparatus and method for performing less-invasive surgical procedures, and more specifically, to a surgical apparatus and method for performing a surgical procedure on the beating heart, such as stabilizing a portion of a beating heart during a coronary artery revascularization, wherein said surgical procedure is performed through a percutaneous transabdominal approach.

BACKGROUND OF THE INVENTION

Cardiac surgery, and more specifically traditional coronary artery bypass graft (CABG) surgery, has been performed since the 1970's on a regular basis with the advent of the cardio-pulmonary machine. In traditional CABG, the patient's heart is exposed by cutting through the patient's sternum and retracting the two halves of the ribcage. The heart is subsequently stopped while the blood continues to be pumped and oxygenated outside the body through extra-corporeal circulation (ECC). The development of the cardio-pulmonary machine for ECC enables surgical interventions to take place on an arrested heart. This allows the surgeon to manipulate and operate on a perfectly still heart. As such, the arrested heart may be positioned to expose and provide the best access to the target artery requiring a bypass grafting.

However, there are two main invasive aspects associated to traditional CABG—the sternotomy incision and the ECC. Even with the constant technological improvements achieved during the last twenty-five years, the advantages offered with ECC have been at times offset by the morbidity (complications) and mortality related to the ECC itself. ECC has been documented to produce some well-known complications. Adverse effects associated with its use continue to be discovered and as such, ECC represents one of the most invasive clinical aspect associated with traditional CABG surgery. The inflammatory response, as well as the systemic microembolisms generated by ECC, induce to some extent a dysfunctional state of the brain, lungs, and kidneys, which tends to increase with the aging of the patient. Furthermore, evidence suggests that when ECC can be avoided, the left ventricular function (pumping efficiency) of the heart is better preserved, thereby also reducing the risks of postoperative complications and the need for ventricular assist devices to wean the arrested heart back to normal function. In addition to being one of the most invasive aspects of traditional CABG, ECC is also responsible for a large percentage of the initial procedure cost of traditional CABG. If ECC-related complications develop, ECC is also responsible for the post-operative costs incurred to treat these complications.

A median sternotomy, although less clinically-invasive than ECC, has the perception of being more invasive due to the surgical scaring that results from the surgery. A full median sternotomy may result in a temporary disturbance in the respiratory mechanism, an increased risk of operative shock or dehiscence, and re-operation surgery from bleeding complications. Moreover, prolonged exposure to air of the exposed mediastinum may lead to hypothermia, infection or compromise of the neuro-endocrine response. Patients with severe chronic obstructive pulmonary disease (COPD), severe emphysema or severe pulmonary insufficiency are therefore at a higher risk of developing complications when exposed to a sternotomy incision.

Port access surgery, developed largely by Heartport Inc. of Redwood City, Calif., consists of replacing the full median sternotomy by a series of intercostal port incisions in the patient's chest, through which coronary artery revascularization is performed. However, the most invasive aspect, ECC, is retained in this type of surgery. The patient's heart is arrested by occluding the patient's aorta preferably between the coronary arteries and the brachiocephalic artery with an expandable balloon on the distal end of an endovascular catheter which may be introduced via a femoral artery. Cardioplegic fluid is then delivered to the patient's myocardium through a lumen in the same catheter or through a separate catheter positioned in the coronary sinus. A series of cannulae and catheters are usually employed to divert the patient's blood flow to the cardiopulmonary machine and to return the oxygenated blood to the circulatory system while the aorta remains occluded to avoid backflow into the heart chambers and surgical field. The port access approach most often also requires lung deflation in order to improve the access to remote territories of the heart, such as the posterior coronary territory. Unlike traditional CABG, the longitudinal axis and apex of the heart cannot be "verticalized" with respect to the surgical table and retracted chest cavity tending to facilitate access to the posterior territory. Performing port access surgery remotely through a number of small ports tends to be difficult, at times leading to unwanted tissue dissection that requires the conversion to a full sternotomy in order to complete the surgical procedure.

In recent years, the drive for less-invasive and cost-effective surgical approaches and apparatus has placed emphasis on cardiac surgery as well. However, unlike other organ surgeries, gall bladder for instance, the beating motion of the heart tends to complicate the surgical intervention.

In minimally invasive direct coronary artery bypass graft surgery (MIDCAB), ECC is avoided and coronary artery revascularization is performed directly on the beating heart with the help of a mechanical coronary artery stabilizer, through a mini-sternotomy or mini-thoracotomy incision. This surgical approach allows access to only one or two of the anterior arteries of the heart, most commonly the left anterior descending artery (LAD). Demographically, only 5-15% of the cardiac surgery population is afflicted with single vessel disease; the majority of cardiac patients (70%) suffer from triple vessel disease, whereby at least one artery on each of the anterior, inferior and posterior territories of the heart requires a bypass graft. As a result, this approach has also been referred to as "limited access bypass surgery". Moreover, the MIDCAB thoracotomy incision to access the beating heart has been discovered to be more painful and less tolerated by patients than originally anticipated, especially in younger patients.

More recently, the beating heart approach through a sternotomy incision has been adopted tending to facilitate positioning of the beating heart within the retracted chest cavity and tending to facilitate grafting of the difficult to access posterior arteries. Mechanical coronary artery stabilizers have been developed to immobilize a portion of the beating heart surface proximate to the target artery during the distal anastomosis phase of the surgery. A median sternotomy is desirable since it tends to allow the apex of the beating heart to clear the retracted ribcage as the heart's longitudinal axis is "verticalized" in order to expose the posterior coronary territory. In some patients, verticalization of a beating heart is not well tolerated and may lead to hemodynamic instability during the surgical procedure. At times, this unnatural "verticalized" orientation of the beating heart may be attained with some degree of atrial or ventricular distortion, and even some degree of valvular dysfunction and regurgitation. Moreover, although the beating heart approach achieves the elimination of the cardiopulmonary machine, the sternotomy incision with its associated complications is retained in this approach.

Percutaneous transluminal angioplasty (PCTA) or Coronary Stenting are intraluminal surgical procedures which achieve coronary artery revascularization through the enlarging of restricted vessels by balloon angioplasty (PTCA) and in some cases also supplemented by the scaffolding effect of the tubular mesh stent. Sternotomy incisions and ECC are avoided since the entire procedure takes place through the patient's artery. However, the high incidence of restenosis associated with PTCA, and its generally low endorsement in the treatment of triple vessel disease does not make this procedure suitable to the majority of cardiac surgery patients that require coronary artery revascularization. Other emerging technologies, such as Transmyocardial Revascularization (TMR) or Percutaneous Myocardial Revascularization (PMR) are reserved for surgically non-reconstructible coronary artery disease.

It would therefore be advantageous to have a surgical apparatus and associated surgical approach which maintains, as much as possible, the normal anatomic position and orientation of the heart during a surgical intervention. One aspect of the present invention aims to provide access to the posterior coronary territory of a beating heart during CABG surgery, without the need for a sternotomy incision, and while the longitudinal axis of the beating heart is maintained as much as possible in its natural, substantially-horizontal anatomic orientation. The combination of the beating heart approach with a surgical approach attempting to access all coronary territories without the need for either a sternotomy or thoracotomy incision would therefore offer distinct advantages in reducing the risk of complications and minimizing the surgical scaring normally associated with current CABG surgeries.

A percutaneous incision in the abdominal region below the patient's ribcage, and the subsequent creation of a trans-abdominal, trans-diaphragmatic tunnel may provide a suitable surgical approach to attain the patient's thoracic cavity. The patient's heart and internal cardiac tissue may then be accessed by a variety of surgical instruments extending through an access cannula placed in said trans-abdominal tunnel and extending beyond an anatomic barrier, such as the patient's diaphragm. A number of surgical manipulations and interventions may then be performed by selected surgical instruments on the target tissue such as the patient's heart or other internal cardiac tissue. Internal cardiac tissue includes but is not limited to the pericardium, epicardium, myocardium, endocardium, apex of the heart, ascending and descending aorta, vena cava, coronary arteries and veins, internal thoracic arteries, pleurae, endothoracic fascia, and other like anatomic tissue.

One aspect of the present invention describes a surgical apparatus that allows the manipulation and positioning of a beating heart within the patient's thoracic cavity, along with the deployment within the patient's thoracic cavity of coronary stabilizers that serve to immobilize a portion of said beating heart proximate to a target coronary artery, through a trans-abdominal tunnel. This aims to allow at least some surgical interventions associated with coronary artery revascularization to be performed without the invasiveness of ECC and without having to perform bone-cutting or bone splitting incisions such as sternotomy, intercostal thoracotomy with spreading of adjacent ribs, or other like surgical incisions. This tends to provide a closed chest surgical approach to perform cardiac interventions. The arteriotomy and distal coronary anastomosis, although may be performed through a number of intercostal ports not requiring the bone splitting or bone spreading incisions, are also preferably performed through the trans-abdominal, trans-diaphragmatic tunnel. In the present invention, the term "closed chest" will refer to surgical procedures which keep the patient's thoracic structure intact.

It is therefore an object of the present invention to provide a surgical apparatus and method that enable coronary artery revascularization on the beating heart without the need for ECC, and without having to spread apart the patient's thoracic bone structure through a sternotomy, thoracotomy or other like incision.

It is a another object of the present invention to provide a surgical apparatus and method that enable cardiac surgical interventions, not restricted to only beating heart CABG, to be performed without having to spread apart the patient's thoracic bone structure through a sternotomy, thoracotomy or other like incision.

Some of the aspects of the present invention may also apply to other types of surgery, such as laparoscopic, endoscopic, or thoracoscopic surgery, whereby surgery is performed on target tissue contained within an internal body cavity that is accessed by surgical instrument disposed through an access cannula. Here the manipulation of surgical instruments during a surgical intervention performed through an access cannula may be better effectuated if said instruments are engaged with an internal joint within said cannula. Also it may be desirable in such surgical procedures to be able to secure said joint and maintain engaged instrument in a desired fixed position and orientation relative to the access cannula, at least for a part of the surgical procedure. The surgical procedure may also be further improved if the access cannula is also engaged with a movable joint connected to a stable surgical platform, whereby said joint may also be secured by a tightening means to maintain access cannula in a desired fixed position and orientation relative to patient and surgical table. The access cannula may also serve to introduce into the internal cavity surgical aids which may not engage target tissue during a surgical intervention, but help facilitate a surgery through their installation. For example, a camera lens or a fiber-optic bundle to provide light.

It is a further object of the present invention to provide a surgical apparatus and method that tends to facilitate endoscopic surgery, more specifically endoscopic surgery where a surgical procedure is to be performed within an internal body cavity beyond an anatomic barrier, through the use of surgical instruments introduced therein through an access cannula.

These and other objects of the present invention will become apparent from the description of the present invention and its preferred embodiments which follows.

SUMMARY OF THE INVENTION

The present invention provides an access cannula with a substantially open proximal end and a substantially open distal end, and at least one substantially hollow passageway extending from said open proximal end to said open distal end. The outer surface of the access cannula is preferably engaged with at least one anatomic barrier. Target tissue is located in an internal body cavity or region downstream of an anatomic barrier and generally beyond the distal end of access cannula. The access cannula provides access, beyond at least one anatomic barrier, to a variety of surgical instruments which are able to extend beyond the distal end of access cannula. Some instruments will engage target tissue during at least a part of the surgical procedure they are intended for.

Instruments are preferably engaged with access cannula through an internal joint which may provide a number of motion degrees of freedom to said instrument when they are engaged with access cannula. Surgical instruments may be demountably engaged with access cannula, or permanently engaged with respect to access cannula, or may even be engaged with access cannula via a cartridge in which they are disposed. Surgical instruments may be secured in a desired position and orientation relative to access cannula and relative to a target tissue through a tightening element.

Proximal end of surgical instruments extend beyond proximal open end of access cannula, thereby allowing the surgeon to manipulate said proximal ends. Proximal manipulations on a proximal end of a surgical instrument, usually applied extracorporeally by the surgeon, are linked through an engagement with an internal joint to distal movements of a distal end of said instrument within an internal body cavity.

The hollow passageway through an access cannula may be partitioned to create additional segregated passageways. Alternatively, substantially longitudinal access lumens extending generally from proximal end to the distal end may also be provided for engagement with surgical aids. Seal members may be provided across hollow passageways in order to maintain an internal body cavity, situated downstream of an anatomic barrier, at a different ambient condition than an extracorporeal region.

Vision ports such as stereoscopic camera lenses, that transmit images to the surgeon so that closed chest interventions may be remotely performed, are deployed within an internal body cavity either through a transabdominal tunnel or through additional intercostal port incisions in the patient's chest. Carbon dioxide is used to displace abdominal organs during the deployment of surgical instruments used to create a transabdominal tunnel. Passages in the access cannula are also provided for the channeling of carbon dioxide gas into the pleural space.

Access cannula may be manipulated and held by hand, but it is preferable to have it engaged with a stable support such as a surgical table. A surgical arm enables access cannula to be reoriented and repositioned relative to a surgical table and also the patient's body. Once a desired position is achieved, access cannula is secured into position.

In performing a beating heart surgery, a variety of different surgical instruments may be engaged with access cannula, some are deployed alone while others may be deployed in combination. In one aspect of the invention aimed to perform coronary artery revascularization on a beating heart, a surgical apparatus is provided comprising an access cannula which is inserted through the diaphragm of the patient such that the distal end of cannula attains the pleural space. A heart manipulator, engaged with an internal joint inside the hollow passageway of access cannula engages the surface of the beating heart, preferably the apex, when said distal end of heart manipulator extends beyond the distal end of access cannula. Once a desired orientation and position of the beating heart is achieved, its position is secured relative to access cannula by an internal joint. A coronary stabilizer, also engaged with an internal joint inside the hollow passageway of the access cannula is then subsequently deployed. Coronary stabilizer is placed on a portion of the surface of a beating heart proximal to a target artery in need of anastomosis. The invention allows the surgeon to position a contact face on the surface of the beating heart and apply a gradual mechanical force until the portion of myocardium around the target artery is stabilized and rendered substantially motionless relative to cannula, while the rest of the heart continues to beat. The coronary stabilizer is subsequently secured. In approaching other vessels of the heart, as in multi-vessel CABG surgery, the access cannula may be rotated about its centerline relative to the heart and body in order to optimize the position of the heart manipulator and coronary stabilizer relative to the target heart tissue. The surgical apparatus aims to provide a way of accessing all territories of the heart by the deployment of an access cannula, and subsequent deployment of a heart manipulator and a coronary stabilizer relative to access cannula and to each other.

Another aspect of the invention describes a surgical method in which the surgical apparatus may be used to perform coronary artery revascularization on the beating heart through an access cannula inserted through a transabdominal approach. This surgical method avoids the ECC and is less invasive for the patient. This surgical method also avoids the need for cutting the patient's ribcage, or spreading apart ribcage or removing part of patient's rib in order to access the patient's heart such as is the case with conventional CABG surgery or beating heart surgery performed through a sternotomy, thoracotomy, or other like incisions.

BRIEF DESCRIPTION OF THE DRAWINGS

For better understanding of the present invention and to show more clearly how it may be carried into effect, reference will now be made by way of illustration and not of limitation to the accompanying drawings, which show an apparatus according to the preferred embodiments of the present invention, and in which:

FIGS. 15A to 15D illustrate the positional relationship between the heart manipulator and the access cannula of FIG. 1;

FIGS. 21A to 21C illustrate a variant of an access cannula in the nature of a removable cartridge comprising internal joints and endoscopic surgical instruments, according to an aspect of the present invention;

DETAILED DESCRIPTION OF THE INVENTION

The features and principles of this invention may be applied, in whole or in part, to other types of cardiac surgery preferably performed through a closed chest approach, and where the patients internal cardiac tissue is attained through a trans-abdominal or trans-diaphragmatic tunnel. Also, the features and principles of this invention may also be applied, in whole or in part, to other endoscopic types of surgery which require access to a target tissue or target organ contained within an internal body cavity, beyond an anatomic barrier, through an access cannula engaged with said anatomic barrier. By way of illustration, the description of the embodiments and variants that follows herebelow will however focus on applying the features and principles of the present invention to cardiac surgery performed on a beating heart, and more specifically, to beating heart CABG surgery.

In the present invention, the term "thoracic cavity" will generally refer to the volume enclosed by the inner surface of the patient's thorax and diaphragm. The term "pleural space" will generally refer to the volume of a thoracic cavity less the space occupied by the mediastinum and the lungs. The lungs normally occupy a large portion of the thoracic cavity. However, deflating a lung during a surgical procedure will augment the pleural space available, within which surgical instruments may be deployed.

Figure 2:
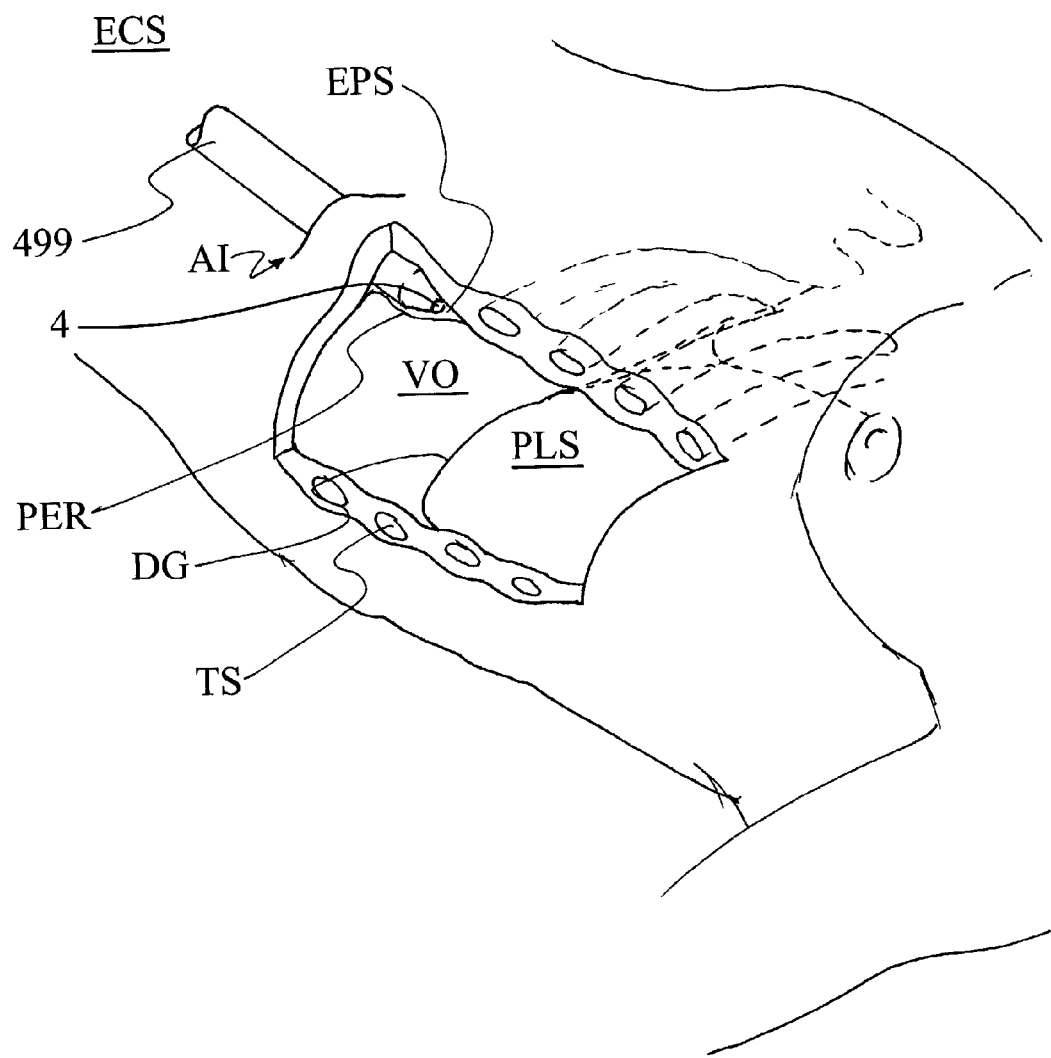
FIG. 2 is a perspective partial cutaway view of the patient illustrating the insertion of a laparoscopic cannula into the abdominal incision to access the pleural space, according to the present invention.
Figure 4:
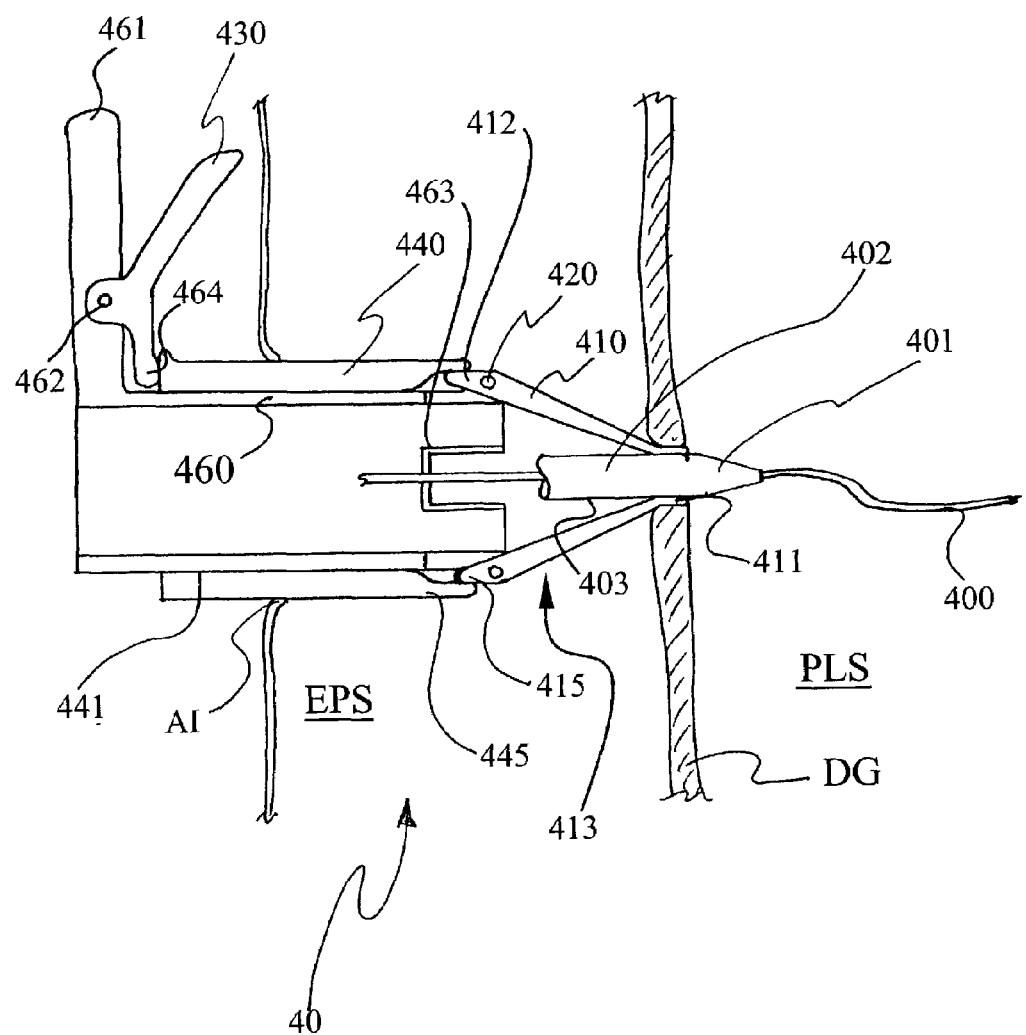
FIG. 4 is a lateral section view of a diaphragm tissue retractor in a closed position engaged with the diaphragm according to an aspect of the present invention.

By way of a general overview and with reference to FIG. 2, a surgical incision is performed in the patient's abdomen (labelled AI), preferably in the left upper quadrant of the abdomen. A laparoscopic cannula 499 is subsequently inserted into the abdominal incision AI, and directed into the underlying extra-peritoneal space (labelled EPS), generally in the direction towards the patient's head. To facilitate the displacement of laparoscopic cannula 499 through the extra-peritoneal space, carbon dioxide gas ($CO_2$) may be channeled through a hollow longitudinal passage in laparoscopic cannula 499 (not shown) and introduced into the extra-peritoneal space through its distal tip 4. This tends to assist the dissection of the extra-peritoneal space and laterally displace the visceral organs (labelled VO) contained within the peritoneom (labelled PER) as the said cannula 499 is advanced within the patient's body. Proceeding in this manner, a sagittal tunnel is created spanning from the site of the abdominal incision to the patient's diaphragm, preferably at the left leaflet location. The diaphragm (labelled DG) constitutes an anatomic barrier that must be traversed in order eventually obtain access to the patient's heart. A guide wire 400 is then inserted through the center of laparoscopic cannula 499 and directed along said cannula 499 through the length of the sagittal tunnel. Once the guide wire 400 exits from the tip 4 of cannula 499, it will be further advanced to pierce the diaphragm and attain the pleural space beyond the diaphragm. The laparoscopic cannula 499 is at this point retrieved from the patient's body leaving behind a guidewire that extends from outside the patient's body, into the abdominal incision, along the sagittal tunnel and beyond the pierced diaphragm into the pleural space (labelled PLS). An enlarging cannula 402 with conical tip 401 and hollow longitudinal passage (not shown) is then channeled over the guide wire 400, through the abdominal incision, through the sagittal tunnel, to attain the diaphragm at the location where said guide wire 400 pierced through the diaphragm. Continuing to advance the enlarging cannula 402 over guide wire 400 will result in conical tip 401 progressively distending and enlarging the hole in the diaphragm initially pierced by guide wire 400, up to a point when the cylindrical surface 403 of cannula 402 becomes engaged with the diaphragm (FIG. 4). Progressively enlarging a hole in body tissue by advancing a cannula configured with a conical tip is usually referred to in the art as a Seldinger Approach.

According to one aspect of the present invention and with reference to FIG. 4, an anatomic barrier tissue retractor in the nature of diaphragm tissue retractor 40 is subsequently inserted over the enlarging cannula 402. The diaphragm tissue retractor 40 is comprised of a substantially cylindrical hollow inner body 460, a plurality of tissue-retracting petals 410, a substantially cylindrical translating sleeve 440, and a deployment lever 430 activated outside the patient's body. The proximal end of inner body 460 is configured with a handle portion 461 extending outwardly away from the longitudinal axis of said inner body 460. The distal end of inner body 460 is configured with a plurality of circumferential slots 463, which provide an opening into which a lug 412 of a retracting petal 410 may pivot when said petal 410 is deployed in the manner described below. Generally one lug 412 is required per petal 410, and one slot 463 is required for each lug 412.

Figure 5A:
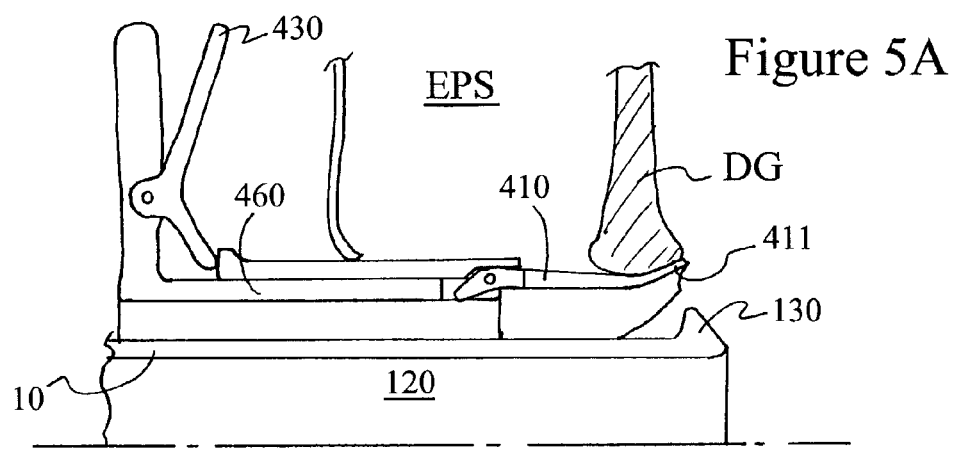
FIGS. 5A and 5B are sectional views illustrating a method of engagement of the access cannula of FIG. 1 with an anatomic barrier.

In their closed, non-deployed configuration, the plurality of tissue retracting petals 410 form a conical leading end profile 413 with a hollow substantially cylindrical tip 411. Tip 411 is well-suited to being insertable and slidable over enlarging cannula 402. Moreover, the conical profile 413 tends to facilitate the advancement of diaphragm tissue retractor 40 through the sagittal tunnel. When the diaphragm tissue retractor 40 is advanced through the patient's diaphragm, hollow tip 411 becomes inserted between the perimeter defining the pierced opening in the diaphragm and the cylindrical surface 403 of enlarging cannula 402. Each petal 410 is rotatingly engaged with the distal end of inner body 460 through a hinge 420 disposed in lug 412. Hinge 420 extends through lug 412 across its circumferential width, and also extends past said circumferential width into the lateral, faces defining circumferential slot 463 in inner body 460. Petals 410, along with their distal end which form a part of said cylindrical tip 411, are then simultaneously deployed through the action of lever 430. Lever 430 is engaged with handle 461 through a hinge 462. A spring element (not shown) may be installed between lever 430 and handle 461 in order to maintain said lever and said handle apart. This minimizes the axial load applied to sleeve 440 thereby biasing tissue retractor 40 in its non-deployed, closed configuration. Deployment is achieved by depressing lever 430 sufficiently to overcome the spring load exerted from said spring element, thereby causing sleeve 440 to axially translate through a sliding fit 441 over the outer surface of inner body 460 and towards the distal end of retractor 40. This entrains the engagement between cam-like surface 445 on translating sleeve 440 and cam-like profile 415 on lug 412 on each of the retracting petals 410. As a result, the translation of sleeve 440 induces a radially inward force on each lug 412 and causes each petal to rotate about hinge 420. The distal ends of retracting petals 410 which are engaged with the diaphragm will consequently be entrained to move outwardly away from the axis of inner body 460 and from one another, thereby retracting the diaphragm tissue in the process (FIG. 5A). The starting aperture in the diaphragm as illustrated in FIG. 4 is enlarged to a desired opening suitable for engagement with the distal end of an access cannula 10.

Unlike the Seldinger Approach, which generally requires a significant length of conical profile to gradually increase the opening in an anatomic barrier by progressive insertion of a conical tip cannula beyond said anatomic barrier, tissue retractor 40 tends to allow the significant enlargement of the diaphragm orifice with minimum risk of injury to the internal cardiac organs lying above and beyond the diaphragm. Significantly greater risk of injury would tend to result if a Seldinger Approach was used exclusively to create an aperture of the desired size in the diaphragm.

Referring again to FIG. 5A, while the diaphragm tissue is maintained in its retracted state by tissue retractor 40, an access cannula 10 is inserted through the center of hollow inner body 460 until its distal end 112 extends into the pleural space beyond the diaphragm. Distal end 112 is configured with an anatomic barrier engaging means in the nature of a permanent weir 130. Permanent weir 130 is preferably rigid, but may also be made from a more flexible biocompatible polymeric material. Weir 130 preferably extends around the entire perimeter of access cannula 10, and in this embodiment extends proudly above surface 113 of said cannula 10. During installation of access cannula 10, weir 130 is inserted past the end of retracting petals 410. Deployment lever 430 is subsequently released, causing petals 410 to close slightly onto surface 113 and diaphragm tissue to contract slightly. Tissue retractor 40 is subsequently retrieved from the patient's body thereby leaving diaphragm tissue engaged with the distal end 112 of access cannula 10, in a location upstream of permanent weir 130.

Figure 3A:
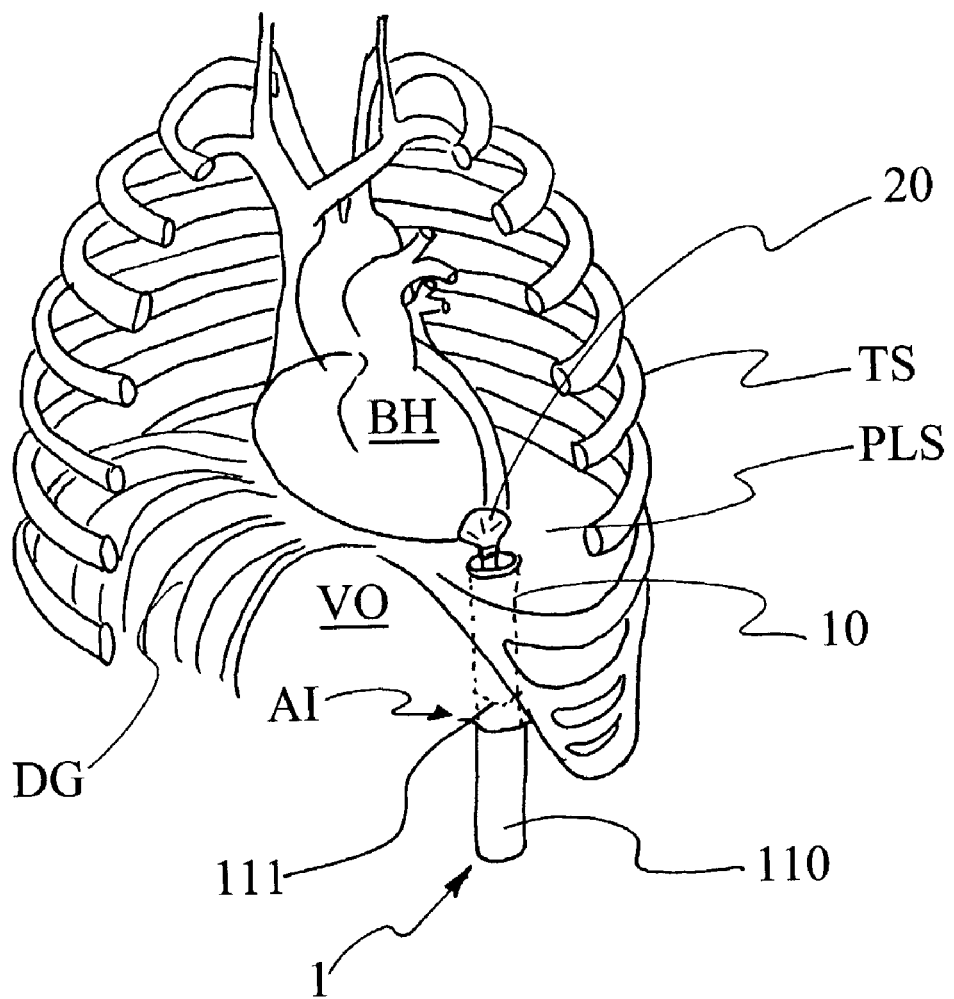
FIGS. 3A and 3B are perspective views of the thoracic cavity illustrating the deployment of the access cannula of FIG. 1.
Figure 3B:
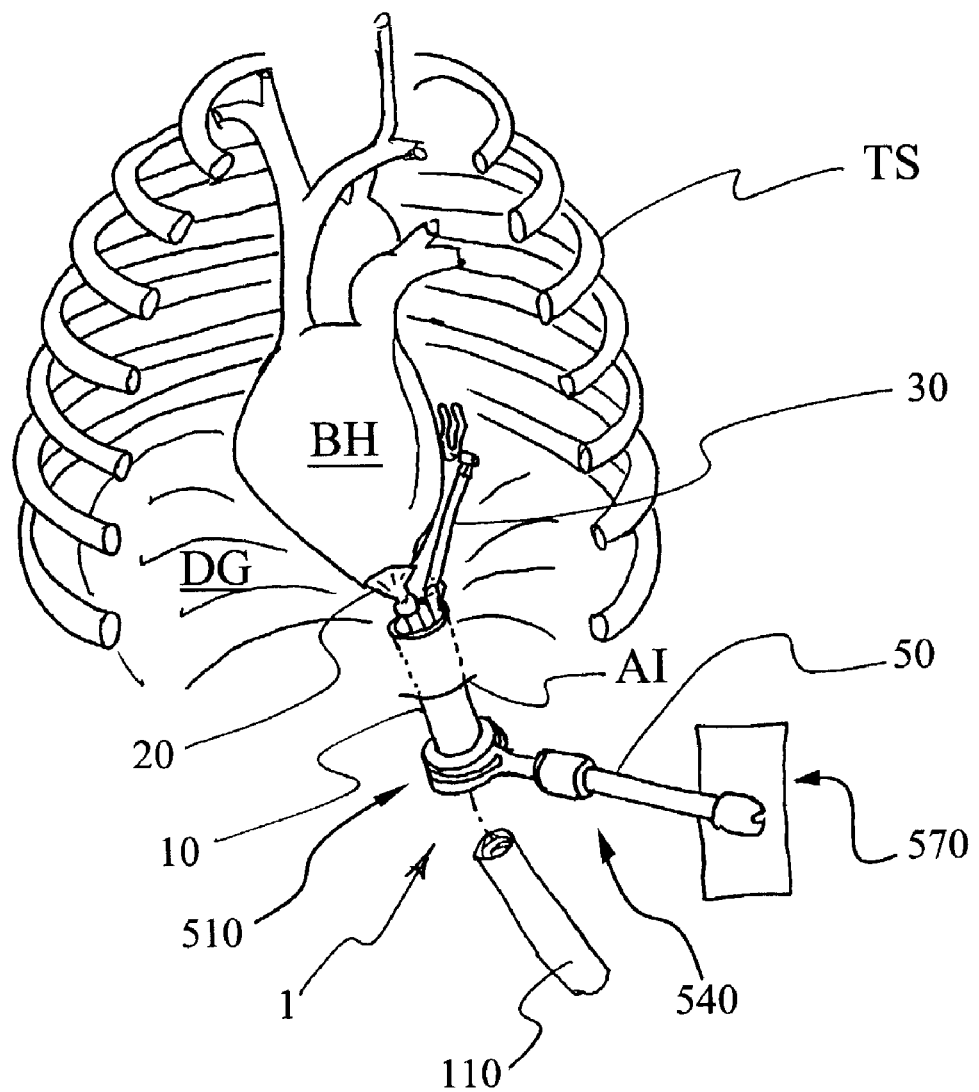

Carbon dioxide gas ($CO_2$) may be introduced into the pleural space and thoracic cavity either through access cannula 10 (as will be described in greater detail below), or through a small intercostal trans-thoracic port incision. This trans-thoracic port incision does not necessitate the cutting or spreading apart of any of the patient's ribs which collectively form the thoracic structure (labelled TS). Pressurized $CO_2$ tends to augment the pleural space and thoracic cavity by pushing down on the dome of the diaphragm. As such, the apex of the heart may be rotated towards the patient's feet into this augmented pleural space (FIG. 3A, 3B). A sealing member, described in greater detail below, may be incorporated within access cannula 10 to substantially maintain the $CO_2$ pressure within the pleural space. When the diaphragm is engaged with the access cannula 10 in a manner as described above, weir 130 acts as an axial abutment face or buttress. The pressure loads on said cannula 10 will maintain it engaged with the diaphragm through the permanent weir 130. Consequently, access cannula 10 may be slightly pushed out of the patient's body at the abdominal incision, leaving a shorter length of access cannula 10 engaged within the sagittal tunnel. Referring to FIGS. 3A and 3B, access cannula 10 may be configured with a demountable proximal extension tube 110. Extension tube 110 serves to facilitate the installation of access cannula 10 into the body. Extension tube 110 also serves to facilitate the positioning and orientation of access cannula 10 relative to the patient's body. Referring to FIG. 3B, extension tube 110 is preferably detached from access cannula 10 once said cannula is engaged with securing platform 50. This tends to improve the ergonomics of the extracorporeal work space. Extension tube 110 is connected to access cannula 10 through a threaded interface 111. Alternatively, extension tube 110 may also be demountably connected to cannula 10 through a bayonet arrangement, a detented arrangement, a wedge fit or of any other like quick assembly interface.

Alternatively, in surgeries where $CO_2$ gas is not introduced into the pleural space, the diaphragm may also be mechanically pulled towards the patient's feet through the abutment face provided by weir 130 when cannula 10 is pulled by the surgeon. Those skilled in the art will appreciate that weir 130 may also be replaced by a circumferential groove, an expandable annular bladder, or any other like means which is capable of engaging the diaphragm through an axial abutment face, preferably configured at the distal end 112 of access cannula 10.

Figure 5B:
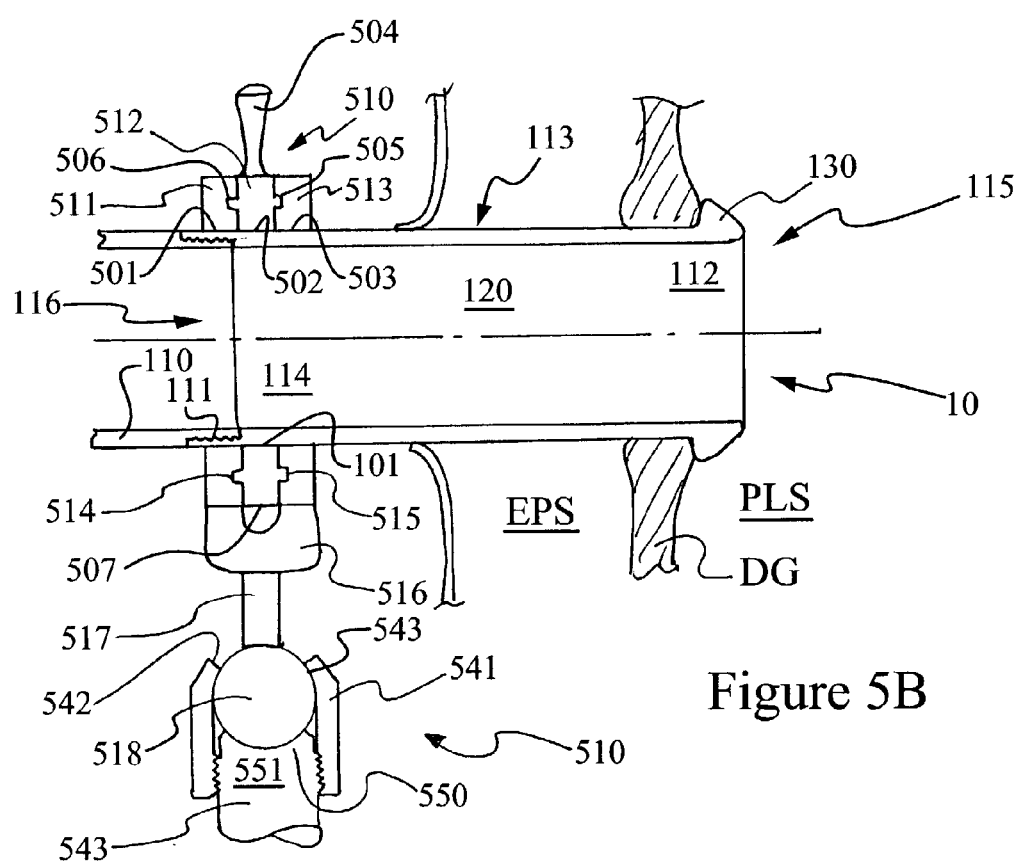
Figure 6:
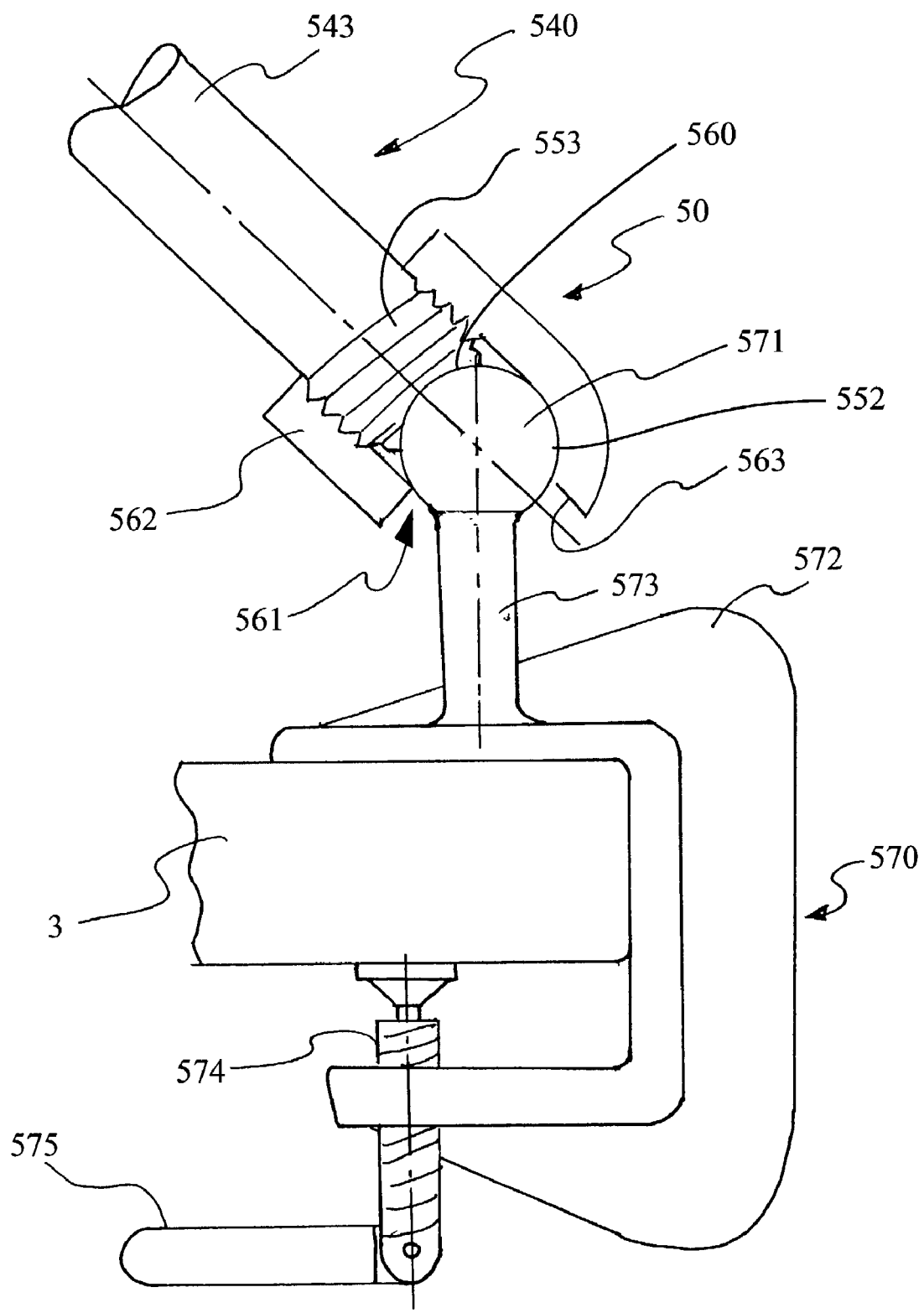
FIG. 6 is a partial lateral section view illustrating the mechanical arm of FIG. 1.

Access cannula 10 may be manually held in position by a surgical assistant during the surgical procedure. However, it is preferable to secure said cannula in a desired substantially stable position and orientation relative to a surgical table 3 or other like fixed stationary support. Referring to FIG. 3B, proximal end 114 of access cannula 10 is secured in place by a mechanical arm 50. Mechanical arm 50 is comprised of a channel clamp 510, an articulation rod assembly 540, and a surgical table clamp 570 (FIGS. 5B and 6).

A preferred embodiment of channel clamp 510 comprises a set of three annular discs 511, 512, 513 whose inner diameters 501, 502, 503 are preferably equivalent. Said inner diameters are only slightly larger than outer diameter 101 of access cannula 10 which extends over a longitudinal portion of its proximal end 114. In a non-deployed state of clamp 510, outer diameter 101 of said cannula 10 is free to slidingly rotate and axially translate relative to inner diameters 501, 502, and 503. Discs 511, 512, and 513 are operatively engaged through annular shoulders 514 and 515 which extend laterally from side faces of disc 512 and engage annular groove 506 in disc 511 and groove 505 in disc 513, respectively. Annular shoulders 514 and 515 are produced with the same eccentricity from the centerline of diameter 502. Annular grooves 505 and 506 are produced with the same eccentricity as annular shoulders 515 and 514. Outer discs 511 and 513 are engaged with disc 512 and permanently connected to each other, with matched eccentricities of annular grooves 506 and 505, through a U-shaped block 516. Said block 516 does not come into contact with the outer surface 507 of disc 512. At one location along its outer surface 507, disc 512 is configured with a lever 504 which extends radially away from said surface 507. Preferably, said lever 504 sits diametrically opposite to U-block 516 when clamp 510 is in its non-deployed state. By moving lever 504 and rotating disc 512 relative to outer discs 511 and 513 will radially offset disc 512 relative to said discs 511 and 513 by virtue of the eccentric interface between annular grooves 505, 506 and annular shoulders 514, 515. Consequently, the three diameter 501, 502, and 503 will place the engaged length of outer diameter 101 in shear, thereby achieving a desired clamping action. Outer diameter 101 will be clamped between a circumferential sector of diameter 502 and diametrically opposite circumferential sectors of diameters 501, 503.

Block 516 is permanently attached to a support rod 517 that has a sphere 518 at the end opposite to block 516. Nut 541 is inserted over rod 517 before it becomes permanently axially retained by sphere 518, once said sphere is permanently mounted to rod 517. Sphere 518 is brought into engagement with socket 550 on threaded end 551 of articulation rod 543 and socket surface 543 within nut 541 when said nut 541 is threaded onto articulation rod 543. When nut 541 is not fully tightened to articulation rod 542, channel clamp 510 is free to rotate and pivot about the center point of sphere 518 within the conical limits defined by the surface 542 of nut 541.

Articulation rod 543 is configured with another socket 560 at opposite threaded end 553. Socket 560 and socket surface 552 within nut 562 are brought into engagement with socket 571 of surgical table clamp 570 when articulation rod 543 is threaded into said nut 562. When articulation rod 543 is not fully tightened to nut 562, articulation rod 543 is free to pivot about the center of sphere 571 within the conical limits defined by surface 563 of nut 562. Sphere 571 is permanently attached to clamp block 572 via rod 573. Nut 562 is inserted over rod 573 before it becomes permanently axially retained by sphere 571, once said sphere is permanently mounted to rod 573.

The location of hole 561 in nut 562 is suitably selected to attempt to provide optimum positioning range for articulation rod assembly 540 and channel clamp 510 with respect to the patient. Clamp block 572 is secured to a surgical table 3 by tightening at least one screw 574 with the aid of a pivoted handle 575.

Those skilled in the art will appreciate that variations of mechanical arms are possible without departing from the spirit of the invention. Alternatively, channel clamp 510 and any other suitable portion of mechanical arm 50 may also be connected to a surgical robot instead of to a surgical table 3.

In summary, mechanical arm 50 is capable of securing access cannula 10 in a desired position and orientation with respect to the patient and to the surgical table 3. Furthermore, mechanical arm 50 enable re-positioning and re-orientation of said cannula 10 during a surgical procedure, without having to disengage said cannula 10 from channel clamp 510. With the channel clamp 510 and nut 541 not fully tightened, the access cannula is free to rotate about its longitudinal axis, translate along its longitudinal axis, and pivot about center of sphere 518. These following motion degrees of freedom are referred to as herein as "coarse adjustment".

Figure 13:
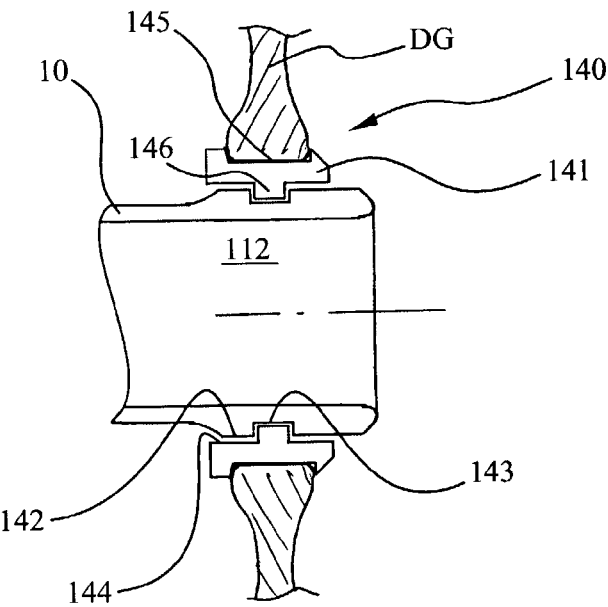
FIG. 13 is a lateral section view illustrating a variant of the diaphragm engagement means of the access cannula of FIG. 1.

In one form of coarse re-adjustment, encountered in surgery such as multi-vessel CABG, it may be desirable to re-orient cannula 10 through a rotation about its longitudinal axis, while said cannula remains engaged with channel clamp 510 at its proximal end and with the diaphragm at its distal end. As described above, placing channel clamp 510 in its non-deployed state will easily allow said cannula to slidingly rotate about its centerline at its proximal end, while engaged in said clamp 510. Referring to FIG. 13, distal end 112 of cannula 10 may be configured with a bearing arrangement 140 to facilitate the said rotation of cannula 10 relative to the engaged diaphragm tissue DG. Bearing arrangement 140 is comprised of an annular cuff 141 which is configured with an external annular groove 145 able to engage the pierced and retracted perimeter of an anatomic barrier, in this case diaphragm tissue DG. Annular cuff 141 is also configured with an internal annular ridge 146 which engages and cooperates with external annular groove 143 in surface 142 of cannula 10. Outer surface 142 of cannula 10 and inner surface 144 of annular cuff 141 are preferably mating cylindrical surfaces allowing annular cuff 141 to be rotatingly engaged with cannula 10. Cuff 141 is axially retained relative to cannula 10 through ridge 146. A desired rotation of cannula 10 about its longitudinal axis will then result in a relative rotation between cuff 141 and cannula 10 while the diaphragm tissue remains fixedly engaged within groove 145 of cuff 141. As such, by virtue of the bearing arrangement 140, the said rotation of cannula 10 tends to limit the torsional load placed on the diaphragm and tends to limit the amount of circumferential slip between the diaphragm and cuff 141 along the engagement perimeter of diaphragm tissue with said cuff 141.

Figure 1:
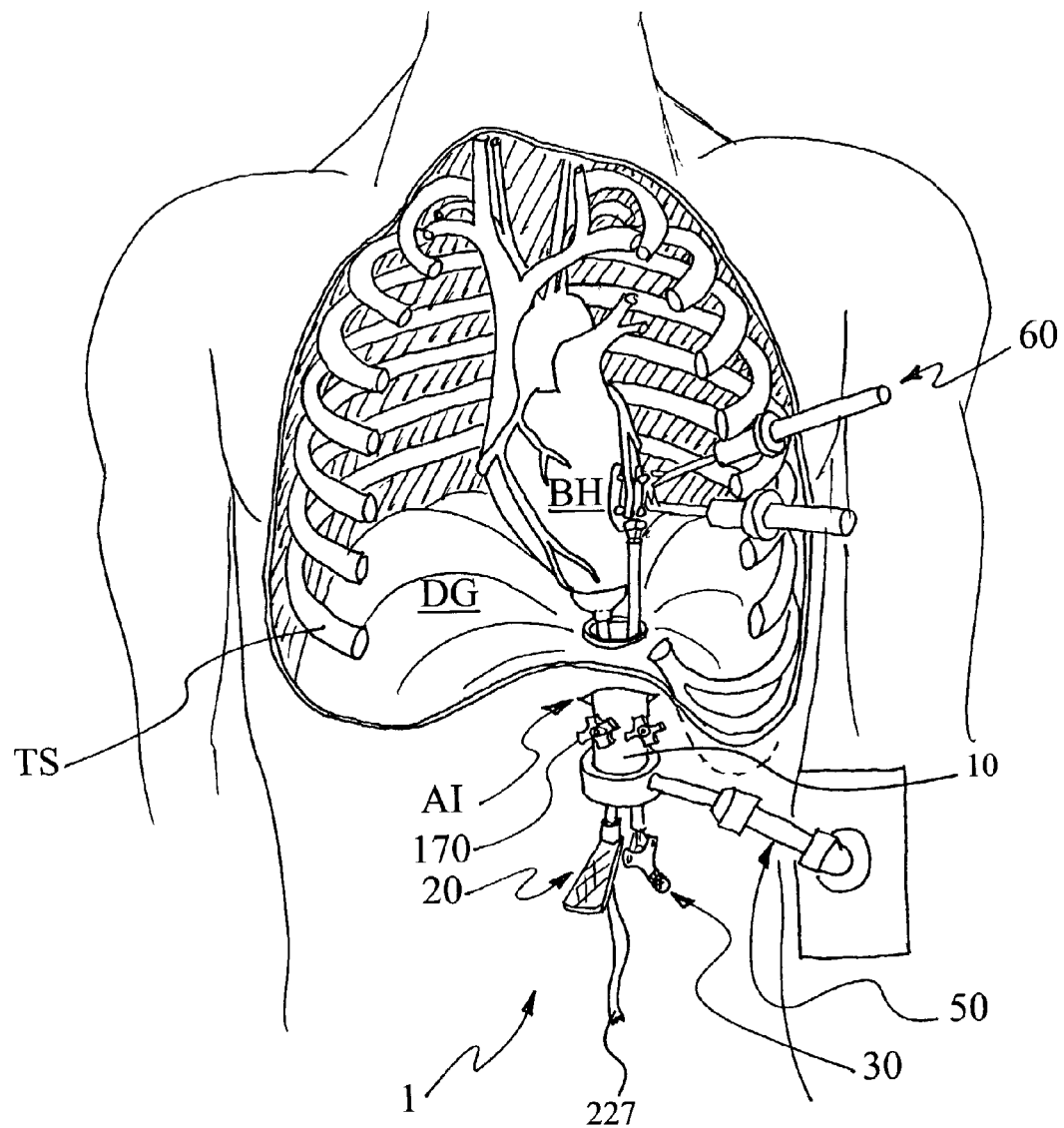
FIG. 1 is a perspective view of a first embodiment according to the present invention illustrating a surgical apparatus for performing beating heart CABG through a transabdominal tunnel.
Figures 16A, 16B:
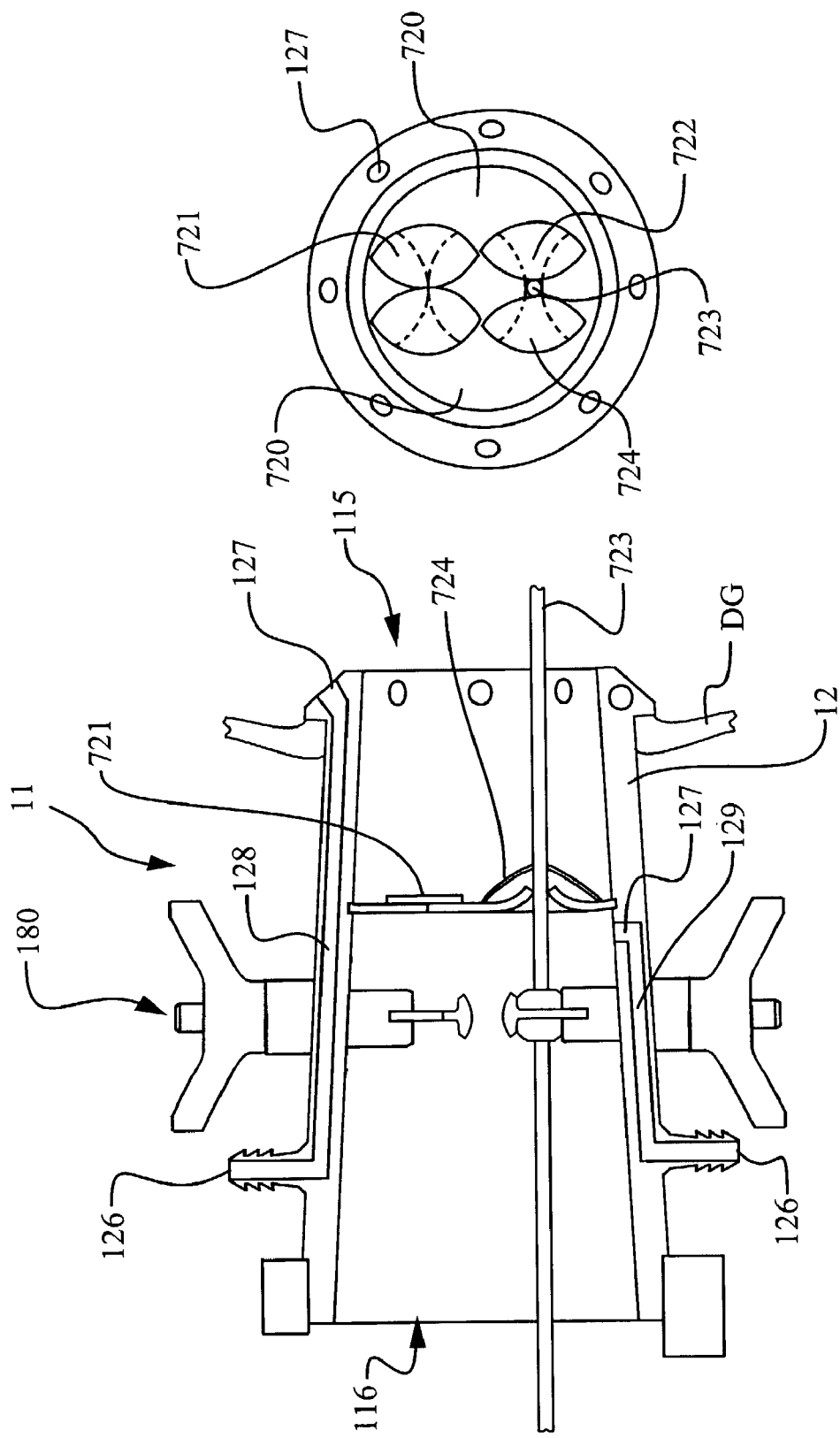
FIGS. 16A and 16B illustrate an access cannula with a variant seal means in the nature of compliant leaflets according to an aspect of the present invention.

Outer surface 113 of access cannula 10 is substantially cylindrical and preferably smooth in order to avoid damage to internal body tissue during its insertion into and removal from patient's body. Referring to FIGS. 1 and 3B, the longitudinal length of cannula 10 is sufficient so that its proximal end 114 extends from patient's body at the site of the percutaneous surgical incision while its distal end 112 is engaged with an anatomic barrier. In this manner the proximal end 114 is exposed and may be engaged with channel clamp 510. Alternatively, an access cannula 11 may be configured with a substantially conical outer surface 12, where preferably the external diameter progressively diminishes from its proximal end 116 towards its distal end 115 (FIG. 16A). Other like tapered configurations are also possible where the overall external dimensions diminish from a proximal end to a distal end.

Substantially open distal end 112 consists of at least one distal opening 115. Substantially open proximal end 114 consists of at least one proximal opening 116. Access cannula 10 is configured with at least one hollow passageway 120 that extends substantially lengthwise along said cannula, from proximal opening 116 to distal opening 115.

When access cannula 10 is deployed within the patient's body, and its distal end 112 is engaged with an anatomic barrier, proximal opening 116 lies upstream of said anatomic barrier, while distal opening 115 lies downstream of said barrier. As such, hollow passageway 120 thereby communicates a region generally upstream of said anatomic barrier with an internal body cavity containing target body tissue, generally downstream of said anatomic barrier, on which a surgical intervention is intended to be performed. For example, access cannula 10 may communicate an extra-corporeal region (labelled ECR) upstream of the patient's diaphragm DG, with the patient's pleural space PLS downstream of said diaphragm DG. A surgical intervention may then be performed on internal cardiac tissue which becomes accessible through hollow passageway 120 of said cannula 10.

As illustrated in FIG. 5B, access cannula 10 is preferably configured to engage the diaphragm at a location close to its distal end 112 with an aim to minimize the protrusion of said distal end into the thoracic cavity. However, in certain surgeries it may be desirable to have an access cannula 10 which engages an anatomic barrier at a location closer to its proximal end 114, even midway between said proximal and distal ends.

In some current endoscopic surgeries, the distal end of an endoscopic surgical instrument is generally manipulated through its proximal handle portion which remains accessible to the surgeon while said endoscopic instrument is inserted into a laparoscopy cannula. Delicate surgical procedures tend to be difficult to master, primarily due to the large unsupported overhang that exists between distal end and proximal end that is grasped by the surgeon's hand. Often times, a compromised tactile sense also tends to result.

Although it is also possible to introduce surgical instrument through access cannula 10 in a similar fashion to a laparoscopy cannula, according to one aspect of the present invention it is preferable to have a surgical instrument engaged with an internal joint 180 disposed within hollow passageway 120 of cannula 10. Internal joint 180 acts as a lateral support member and serves to minimize the overhang between the proximal end and the distal end of a surgical instrument engaged therein. Internal joint 180 is free to move when engaged with a surgical instrument prior to being secured into a fixed position through a tightening member 181. When said internal joint is secured, it may serve to retain a surgical instrument engaged therein in a fixed position and orientation relative to access cannula 10. As will be explained further below, internal joint 180 may also act as a fulcrum member. By virtue of the fulcrum member, a surgeon input applied to a surgical instrument at its proximal end will be transferred to its distal end, whereby the resulting movement of the distal end may be of an equal magnitude, greater magnitude, or a lesser magnitude relative to said surgeon input.

Figure 14A:
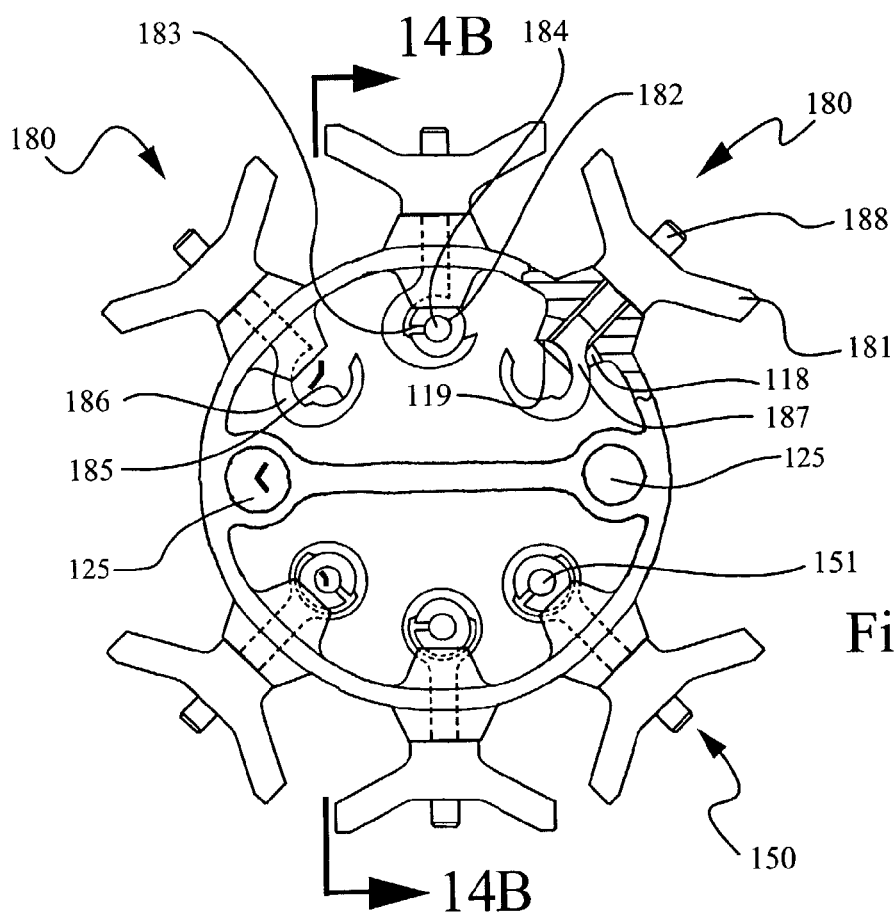
FIGS. 14A to 14C illustrate variants of internal joints and seal means in the nature of a radial bellows according to an aspect of the present invention.
Figure 14C:
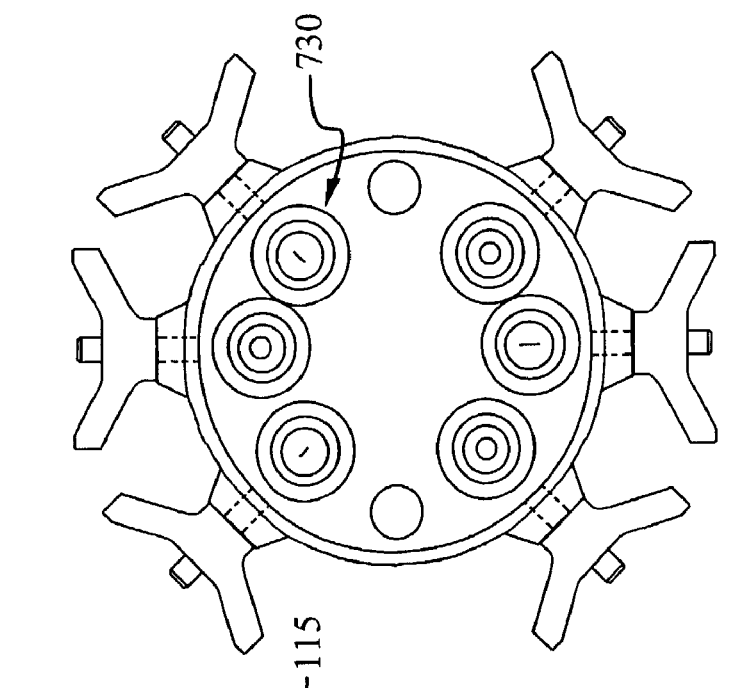
Figure 14B:
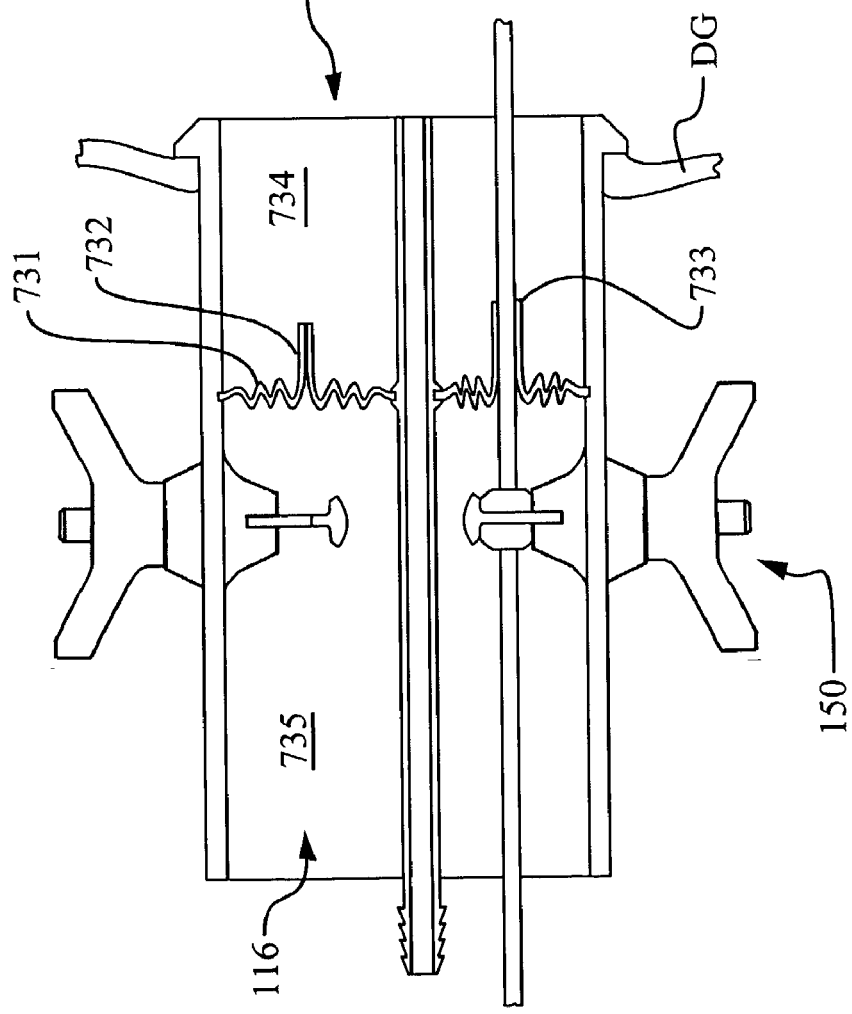

Referring to FIGS. 14A and 14B, at least one internal joint is provided within the at least one hollow passageway 120 in access cannula 10. Internal joint 180 protrudes away from the internal surface of hollow passageway 120 so that it may become engaged with a portion of a surgical instrument. Internal joint 180 is comprised of a substantially spherical collet 182, a yoke 186, and a tightening member 181. Said collet 182 is configured with a cylindrical bore 184 whose centerline coincides with the center of spherical collet 182. Said collet 182 is configured with at least one split gap 183 extending from its outer spherical surface to inner cylindrical surface defining bore 184. Said split gap 183 preferably extends throughout the entire longitudinal length of said bore 184. Alternatively, collet 182 may be configured with a plurality of like split gaps as those skilled in the art will appreciate. Collet 182 is preferably made from a substantially elastic material.

A surgical instrument may first be inserted into bore 184 of spherical collet 182, and the resulting assembly thereof transversely installed into yoke 186. In this respect, internal joint 180 is considered an "open-ended design" since it permits a surgical instrument to be transversely mounted into engagement with inner joint 180. Alternatively, spherical collet 182 may first be engaged into yoke 186 and a surgical instrument subsequently installed axially through bore 184 thereof. Yoke 186 is configured with a spherical seat 185. Extension rod 189 is provided with an anti-rotation flat 187 which cooperate with opening 118 when said rod is inserted through said opening. Tightening member 181 engages with thread 188 on the distal end of extension rod 189.

Collet 182 simultaneously cooperates with socket surface 119 of access cannula 10 and spherical seat 185 of yoke 186, when internal joint is fully assembled. Applying a torque to tightening member 181 will entrain seat 185 into light contact with spherical collet 182, and spherical collet 182 into light contact with socket surface 119. At this point, a surgeon manipulation (input) applied to the proximal end of surgical instrument will be easily sufficient to set into relative motion spherical collet 182 relative to socket surfaces 185 and 119 (free state). Applying a greater torque to tightening member 181 will augment the friction between external surface of collet 182 and said spherical surfaces 185 and 119, thereby providing a greater resistance to the surgeon input (constrained state). Increasing the tightening torque still further will compress spherical collet 182. The resulting compression force is transferred to the portion of a surgical instrument engaged within bore 184 as a clamping load by virtue of split gap 183, thereby securing the entire assembly of components defining internal joint 180 (locked state). Relieving the tightening torque on tightening member 181 will relieve said clamping load on said surgical instrument and relieve the friction between socket surfaces 119, 185 and spherical collet 182. The internal joint 180 resumes its free state, aided in part by the elastic nature of collet 182. At this point, said surgical instrument is once again free to be re-positioned and reoriented with respect to access cannula 10 through internal joint 180.

The portion of a surgical instrument engaged within bore 184 is preferably of circular cross-section. The internal joint 180 provides the following motion degrees of freedom when engaged in "free state" with a surgical instrument: translation of said surgical instrument along centerline of bore 184, rotation of said surgical instrument about centerline of bore 184, pivoting of said surgical instrument about a longitudinal axis through extension rod 189, pivoting of said surgical instrument about an axis perpendicular to longitudinal axis through extension rod 189 and simultaneously perpendicular to centerline of bore 184. Open-ended internal joint 180 allows 4 motion degrees of freedom and may be secured through tightening member 181 which is situated on the exterior of access cannula 10. These motion degrees of freedom between a surgical instrument and access cannula 10 are referred to herein as "fine adjustments". Alternatively, a surgical instrument with one or more integral spherical bosses along its longitudinal axis may be inserted into internal joint 180 in place of spherical collet 182.

Open-ended internal joints permit the substitution of surgical instruments engaged with said joints, without having to disrupt the coarse adjustment of the surgical set-up.

Other variations of internal joints may be configured as those skilled in the art will appreciate, some with fewer motion degrees of freedom. For instance, a joint that only allows translation along the longitudinal axis of a surgical instrument, a joint that only allows rotation of a surgical instrument about its centerline, a joint that only allows pivoting about one axis, and any combination thereof represent potential embodiments.

A close-ended variant of the internal joint 180 is illustrated in FIGS. 14A and 14B. Close-ended joint 150 is preferably employed to engage surgical instruments that form an integral permanent assembly with an access cannula. Alternatively, in non-permanent assemblies, close-ended joints may also be employed with surgical instruments having cross-sectional dimensions inferior to bore 151, which are therefore capable of being axially inserted through said bore.

Figure 8:
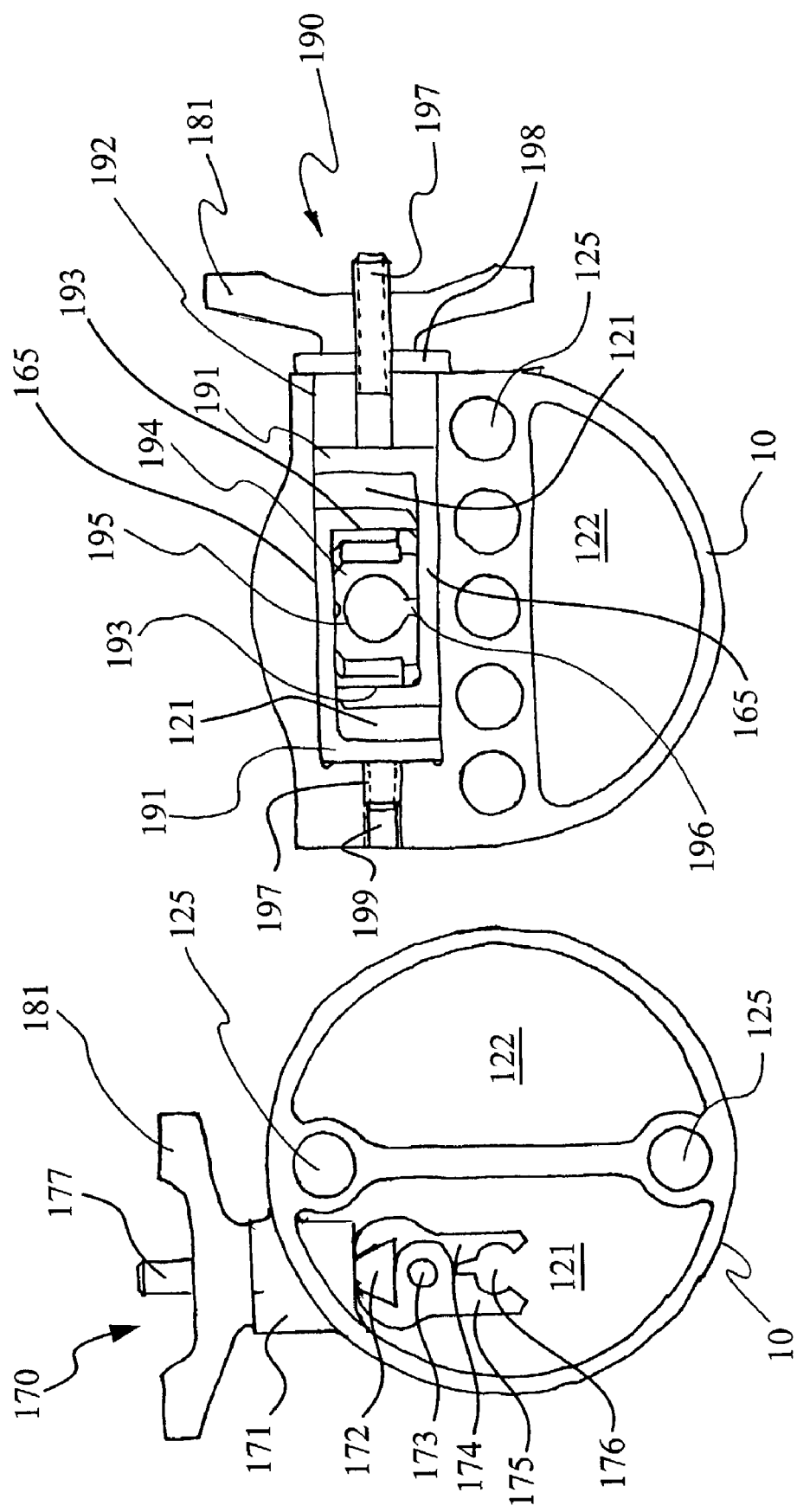
FIGS. 8A and 8B are end views illustrating several variants of access cannulae and variants of the internal joints according to the present invention.

FIG. 8A illustrates another variant of an open-ended internal joint 170. Internal joint 170 is comprised of two jaws 174, 175 which are pivotingly engaged through hinge member 173. Said jaws cooperate to clamp a surgical instrument at open-ended bore 176 when wedge 172 is retracted through hollow boss 171 through its connection to threaded rod 177. Applying a tightening torque to tightening member 181 will entrain threaded end 177 to move axially through hollow boss 171. Prior to applying a securing torque to said member 181, jaws 174, 175 are free to rotate about the centerline of threaded rod 177. Inner joint 170 provides the following motion degrees of freedom: translation of a surgical instrument along the longitudinal axis of bore 176, rotation of a surgical instrument about centerline of bore 176, and rotation about centerline axis of rod 177.

Another close-ended, multi-degree of freedom variant of an internal joint is illustrated in FIG. 8B. Internal joint 190 is comprised of two C-shaped jaws 191 and an articulation cylinder 194. Each jaw 191 has a threaded rod 197 extending along its longitudinal axis. Each jaw 191 has a substantially hemi-cylindrical surface 193 defined by an axis perpendicular to its longitudinal axis. Each jaw has a lateral member 165, offset from longitudinal axis of said jaw, connecting threaded rod 197 to surface 193. When jaws 193 are assembled with articulation cylinder 194, threaded rods 197 extend in opposing directions through a common centerline, each of surfaces 193 lie diametrically opposed, and each of lateral members 165 are laterally opposed. Articulation cylinder 194 is laterally trapped between said lateral members 165 and radially engaged with each of the hemi-cylindrical surfaces 193. A cylindrical bore 195, perpendicular to the centerline of cylindrical outer surface of articulation cylinder 194, is provided to receive a portion of a surgical instrument axially inserted therein. The inner surface of cylindrical bore 195 is interrupted by at least one substantially longitudinal split 196.

When assembled jaws 193 are assembled, outboard surfaces of lateral members 165 form a partial interrupted cylinder whose centerline is coincident with centerline of threaded rods 197. The assembly comprised of jaws 191 and articulation cylinder 194 is transversally inserted into bore 192 of access cannula 10. Threaded rod 197 of one of the jaws 191 is sufficiently threaded into boss 199 of cannula 10 such that centerline of bore 195 is substantially aligned with longitudinal axis of access cannula 10. At least a portion of said cylinder formed by outboard surfaces of lateral members 165 cooperates with bore 192 as internal joint 190 rotates within said bore 192. As internal joint 190 rotates within bore 192 threaded rod threads or unthreads itself into boss 199. Said bore 192 is mostly open towards the center of access cannula 10 providing substantially unrestricted motion to a surgical instrument engaged in bore 195 of articulation cylinder 194. Washer 198 is inserted between access cannula 10 and tightening member 181. A tightening torque applied to tightening member 181, will entrain into contact said hemi-cylindrical surfaces 193 with outer diameter of articulation cylinder 194. A substantially diametrical clamping load will be applied to outer diameter of articulation cylinder 194. The resulting compression force is transferred to the portion of a surgical instrument engaged within bore 195 by virtue of split 196, thereby securing the entire assembly of components defining internal joint 190.

Internal joint 190 allows the following motion degrees of freedom: translation of a surgical instrument along centerline of bore 195, rotation of a surgical instrument about centerline of bore 195, pivoting of a surgical instrument about centerline through bore 192, pivoting of a surgical instrument about an axis perpendicular to centerline through bore 192 and simultaneously perpendicular to centerline of bore 195. Once the desired position and orientation of a surgical instrument is achieved, this fine adjustment is secured through tightening member 181 situated on the exterior of access cannula 10.

Internal joints 150, 170, 180, and 190 may engage the particular surgical instruments according to the present invention, and also existing endoscopic instruments, laparoscopic instruments, cardiac surgery instruments and other like instruments.

Figure 20:
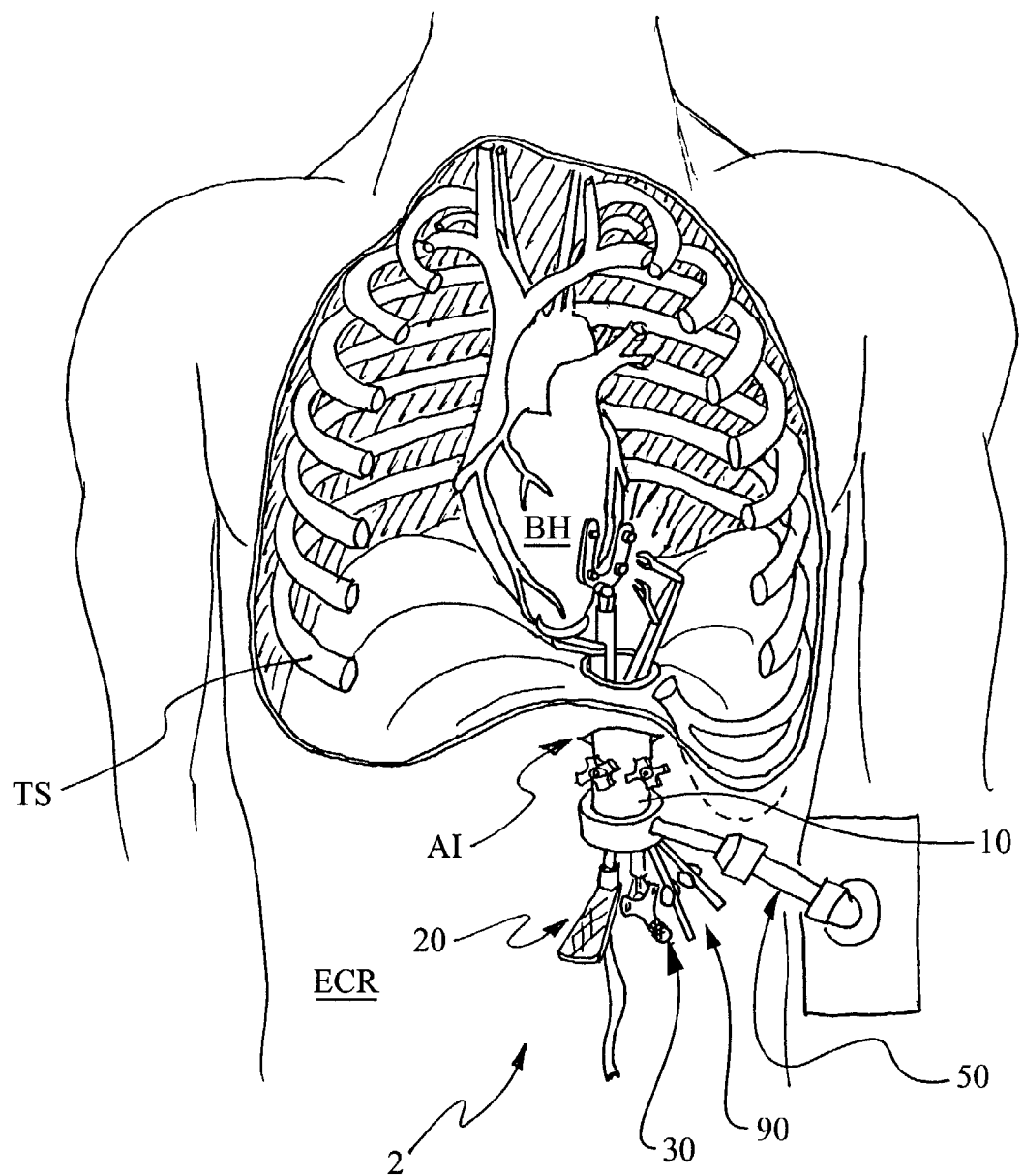
FIG. 20 is a perspective view of a second embodiment according to the present invention illustrating a surgical apparatus comprised of an access cannula, a heart manipulator, a coronary stabilizer, and a variety of endoscopic surgical instruments according to the present invention;.

Internal joint 180 acts as a fulcrum point allowing the movement at the proximal end of a surgical instrument (surgeon input) to be transferred through internal joint 180 to a corresponding linked movement at the distal end of said surgical instrument. For the purposes of illustration, FIG. 20 schematically represents access cannula 10 as a cylinder. An internal joint is located within access cannula 10 at a distance X from proximal open end 116 and at a distance Y from the center line of access cannula 10. A surgical instrument is schematically represented as a line (labelled "SI"). PSI represents the surface area within which a surgeon may position a proximal point P of a surgical instrument, when said point P is held at a fixed distance from the center of the internal joint. When point P is held at a closer distance from the center of internal joint, PS2 is generated. DS1 and DS2 represent the surface areas within which the distal point D of a surgical instrument is maintained during proximal manipulations of point P within PS1 and PS2, respectively. The size and geometry of proximal surfaces PS1 and PS2 and of distal surfaces DS1 and DS2 are a function of the specific geometry of access cannula 10, the number of motion degrees of freedom offered by the internal joint, the range of motion of said offered motion degrees of freedom, the length of surgical instrument SI, and the distance between proximal point P on surgical instrument SI and internal joint. If a surgeon's input is applied to proximal point P and is limited to the confines of proximal surface PS1, distal point D will then be limited to the confines of distal surface DS1. As illustrated in FIG. 20, since proximal surface PS1 is larger than corresponding distal surface DS1, a surgeon input applied at point P will result in a scaled down output at point D. Alternatively, if a surgeon's input is applied to proximal point P and is limited to the confines of proximal surface PS2, distal point D will then be limited to the confines of distal surface DS2. Since proximal surface PS2 is smaller than distal surface DS2, a surgeon input applied at point P will result in a scaled up output at point D. Therefore, a surgeon input applied extracorporeally to a proximal end of a surgical instrument will entrain a linked movement of a distal end within an internal body cavity, downstream of an anatomic barrier by virtue of an internal joint.

Hollow passageway 120 may be partitioned to define at least one other hollow passageway extending from proximal open end 116 to distal open end 115. Two such hollow passageways 121, 122 are illustrated in FIG. 8A. At least one such passageway will be configured with an internal joint such as 150, 170 180, 190 or other like joint or variant thereof. In other surgical set-ups, it may be preferable to have at least one internal joint in each of the said hollow passage ways 121, 122. The relative cross-sectional areas and cross-sectional geometries of partitioned hollow passageways may be tailored for the specific surgical instrument said passageway will be engaged with, or the specific surgical procedure that will take place in said passageway. In general, a hollow passageway is intended to be engaged with a surgical instrument. In configurations of access cannulas comprising more than one internal joint, said internal joints may each be disposed at a different location along the longitudinal axis of said cannula, and each be disposed at a different angular orientation relative center of longitudinal axis.

In addition to hollow passageways, access cannula 10 may be configured with one or more access lumens 125 (FIGS. 8A, 8B, 14A). Access lumens provide a substantially confined channel into which a surgical aid, fluid, or gas may be engaged or introduced.

Each access lumen may serve a designated purpose during at least a part of a surgical procedure or may be specifically designed to engage a particular surgical aid for the duration of the surgical process. An access lumen may be integrally produced with access cannula 10 as a cored passage in the fabrication process. Alternatively, an access lumen may be formed from a channel member which is subsequently fastened to access cannula 10, preferably within one of its hollow passageways. Access lumen may be fastened in a demountable or permanent manner to said access cannula 10. Access lumens have at least one entry point 126 and at least one exit point 127. Generally, access lumens extend from proximal open end 116 to distal open end 115 of cannula 10. However, they may extend for only a part of the longitudinal length of cannula 10. In either case, entry point 126 is generally located upstream of anatomic barrier and 127 is generally located downstream of anatomic barrier. This provides a communicative channel from a region upstream of said anatomic barrier (most often the extracorporeal space ECS) to an internal body cavity such as the pleural space PLS.

In another variant, an access lumen may extend for only a part of the longitudinal length of cannula 10, where entry point 126 and exit point 127 are either both upstream of anatomic barrier or both downstream of an anatomic barrier.

In another variant, an access lumen 129 is configured with an exit point 127 leading into the at least one hollow passageway of access cannula 10 (FIG. 16A).

In another variant, access lumen does not longitudinally along length of access cannula 10, but may be of a helical configuration along the surface of hollow passageway 120.

In yet another variant, access lumen 128 may be configured with a circumferential segment acting as a manifold for a plurality of exit holes 127 (FIGS. 16A, 16B). This configuration may be preferable for introducing a surgical gas such as CO2 into the pleural space.

Designated access lumens may be provided for engaging following surgical aids, or channeling the following fluids or gases: a malleable arm with small atraumatic clip at distal end thereof, a fiber optic bundle for illumination of surgical site, a surgical camera lens, CO2 pressurized gas, saline solution, pharmacological agents, a suction line, a catheter, a cannula, a laser probe, a doppler ultrasonography probe, a sensor, or any other like surgical aid, fluid or gas.

A visioning system may be housed in an access lumen to allow the surgeon to vision the substantially closed pleural space (or thoracic cavity) during the surgical procedure performed therein. A visioning system is preferably comprised of stereoscopic camera lenses. In another variant, only some of the components of the vision system may be provided in an access lumen while other complimentary components may access the substantially closed thoracic cavity through intercostal access ports. Also in this manner separate vision cameras may be configured, one in an access lumen of access cannula 10, another in an intercostal port incision, thereby allowing the surgical procedure within the thoracic cavity to be visioned through one or more different visual perspective.

Access cannula 10 may be configured with a combination of internal joints, partitioned hollow passageways, and a number of access lumens. For instance, FIG. 8A illustrates a partitioned access cannula 10 with one open-ended internal joint 170, two hollow passageways 121, 122 and two access lumens 125. FIG. 8B illustrates a partitioned access cannula 10, with one close-ended internal joint 190, two hollow passageways 121, 122, and a plurality of access lumens 125. FIG. 14A illustrates a partitioned access cannula 10 with a plurality of close-ended internal joints 150 and a plurality of open-ended joints 180, two hollow passageways 121, 122 and two access lumens 125. Other combinations are also possible.

Access cannula 10 may be configured with a provision for a sealable hollow passageway. A seal member 70 may be provided to span in a substantially transverse manner across a hollow passageway. Seal member 70 will preferably span across hollow passageway at a location between proximal open end 116 and distal open end 115 of said cannula 10. Seal member 70 may also span across proximal open end 116 or distal open end 115.

Seal member 70 provides a substantial seal and substantially confines the ambient conditions present within the internal body cavity and within a hollow passageway downstream of said seal member, from the ambient conditions present in the hollow passageway upstream of said seal member and externally beyond the proximal open end 116 of said access cannula 10. For instance, in surgeries where CO2 gas will be introduced into the pleural space PLS, the pressurized volume present within the pleural space and within a hollow passageway of access cannula 10 downstream of seal member 70 is substantially confined from the extracorporeal ambient conditions present upstream of said seal member. Evidently, to maintain said pressurized volume all hollow passageways must be provided with a seal member 70, and all access lumens must also be substantially sealed either with a plug member engaged at entry point 126 or exit point 127, or by the obstruction created by a surgical aid engaged within said access lumen, or by a seal member similar to seal member 70.

Seal member 70 may also be used to shield a portion of a hollow passageway and internal joints located upstream of said seal member from blood and other like body fluids present within the internal body cavity and downstream of said seal member. In a partitioned access cannula, a seal member may be provided in just one of the hollow passageways, or in all said passageways.

Figure 7:
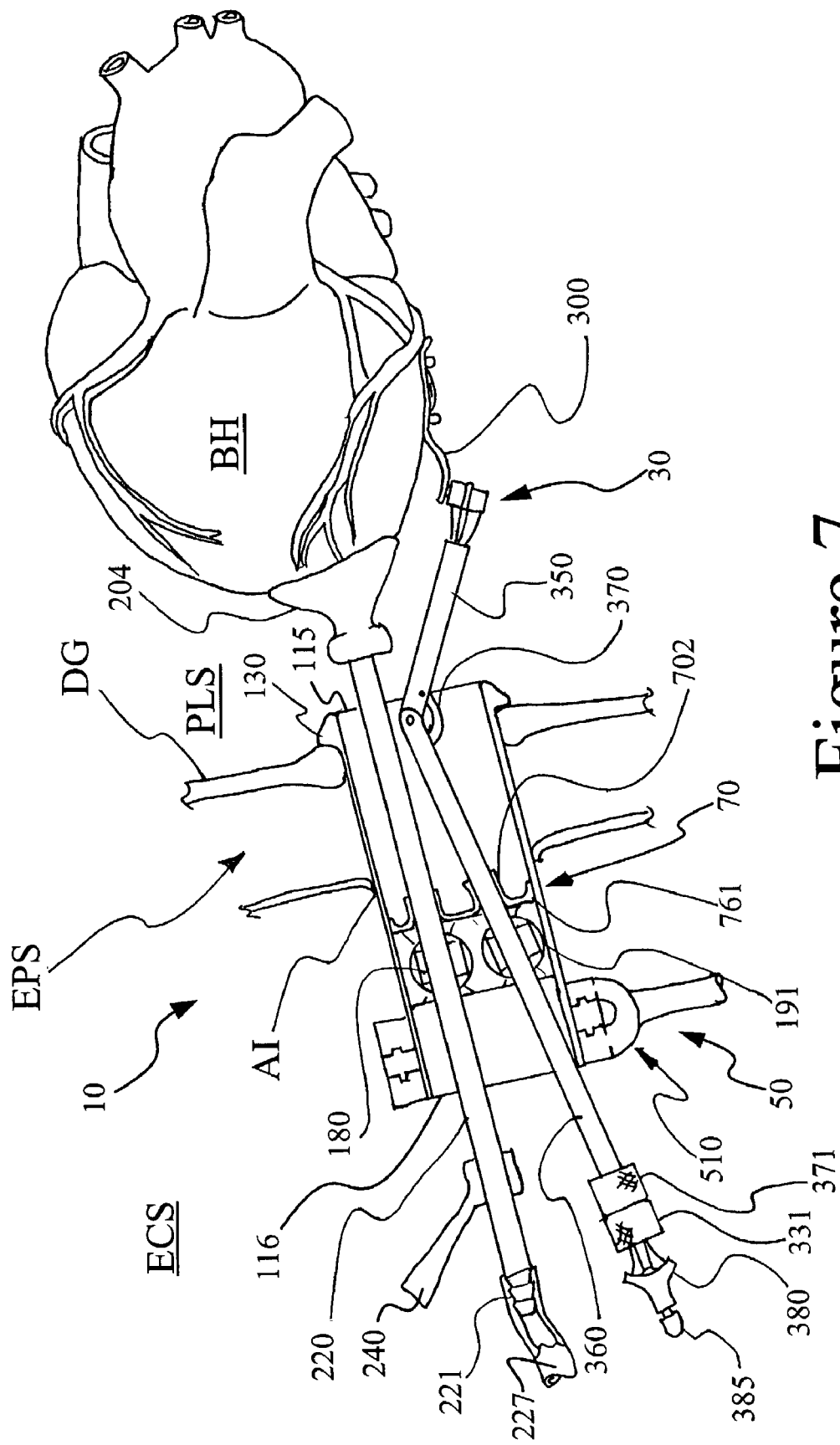
FIG. 7 is a lateral cross section view illustrating the heart manipulator, coronary stabilizer, and access cannula of FIG. 1 engaged with the beating heart and the diaphragm.

FIG. 7 illustrates a conformable elastic seal membrane 701. Seal membrane 701 is provided with one or more sealable ports in the nature of elastic nipple 702 through which a variety of surgical instruments may be easily inserted either before or during surgery. Elastic membrane 701 and nipple 702 will conform to suit the angle in which the shaft portion of a surgical instrument will be oriented within said nipple. This tends to provide substantially unconstrained motion of the surgical instrument within access cannula 10. Further, elastic nipple 702 provides a compliant through-passage that stretches and shrinks to accommodate surgical instruments with different dimensions. Elastic nipple 702 is biased towards a closed, sealed position wherein said variable size through-passage is not engaged with a surgical instrument. Said nipple 702 is movable to an open, sealed position by virtue of inserting a surgical instrument therethrough. As such, elastic nipples 702 provide a substantial seal in both closed and open position.

FIGS. 14B and 14C illustrate a conformable, elastic bellows-type seal 730. Seal 730 is comprised of a plurality of elastic nipples 732. Nipples 732 are self-energizing in that a pressure gradient will keep nipple closed and substantially non-flowing when surgical instrument is not engaged therein. When a surgical instrument is inserted in said nipple 732, the self-energizing effect will keep nipple perimeter 733 in contact with surgical instrument. Pressure gradient for self-energizing effect requires the pressure downstream of nipple perimeter in region 734 to be greater than pressure upstream of seal in region 735. As illustrated, seal 730 is self-energizing when pressurized $CO_2$ is introduced into the pleural space. Seal 730 may be reversed to cater for opposite pressure gradients. Nipple 732 provides a substantial seal.

Seal 730 is configured with a plurality of substantially concentric annular folds 731 originating from the center of each nipple 732. Said plurality of annular folds 731 act as a radial bellows. A displacement of nipple 732 entrained by a movement of a surgical instrument relative to cannula 10, will compress annular folds 731 in the direction of said displacement of nipple 732. By virtue of its elastic material properties and its radial bellows configuration, seal 730 tends to allow substantially unconstrained motion of a surgical instrument within access cannula 10.

FIGS. 16A and 16B illustrate an elastic membrane-type seal 720 provided with one or more sealable ports in the nature of a plurality of overlapping leaflets 724 through which a variety of surgical instruments may be inserted. Said leaflets 724 are biased in a closed, not deflected orientation 721 thereby providing a substantial seal. When instrument is inserted through said sealable port, leaflets 724 are deflected 722 but remain in substantial contact with the shaft portion 723 of a surgical instrument. As such, leaflets 724 provide a substantial seal in both closed and deflected position. Leaflets will engage with shaft portion 723 to a varying extent depending on the orientation of said shaft portion 723 through said leaflets 724. All leaflets will be engaged to at least some extent, throughout the complete range of orientations said shaft portion 723 is capable of assuming in order to maintain a substantial seal throughout said range. By virtue of its elastic material properties and its leaflet configuration, seal 720 tends to allow substantially unconstrained motion of a surgical instrument within access cannula 10.

By way of a general overview, FIG. 1 illustrates a surgical apparatus according to a first embodiment of the present invention. The surgical apparatus is comprised of a surgical arm 50, an access cannula 10, a heart manipulator 20, and a coronary stabilizer 30. Thoracoscopic surgical instruments 60 are provided with which the invention may be used. Said instruments 60 are deployed intercostally and tend to not require spreading of the patient's ribcage. Access cannula 10 is preferably deployed and engaged with the patient's diaphragm through diaphragm tissue retractor 40 in a manner described above.

Referring to FIG. 7, heart manipulator 20 and coronary stabilizer 30 are preferably engaged with access cannula 10 through an internal joint 190 (or alternatively 150, 170, or 180), in a manner already described with general reference to a surgical instrument.

Once the coarse adjustment has been performed and access cannula 10 has been secured to channel clamp 510 of surgical arm 50 in the desired position and orientation relative to the patient's body, the heart manipulator 20 is preferably deployed first.

Heart manipulator 20 engages a portion of the surface of a beating heart, preferably in the vicinity of the apex, through a negative pressure suction force. Said manipulator 20 serves to position and orient the patient's heart within the thoracic cavity. While it is engaged with the apex of the patient's heart, heart manipulator 20 may be secured through internal joint 190 in a desired position and orientation relative to access cannula 10 (fine adjustment), thereby also securing a position and orientation of the patient's heart relative to said access cannula 10.

Heart manipulator 20 is comprised of a hollow shaft member 220, a heart contacting member 200 and a handle 240. Shaft member 220 is preferably cylindrical in cross-section and hollow thereby configuring conduit 223 along its entire length. Shaft member 220 is engaged at its distal open end 226 with heart contacting member 200 and at its proximal open end 224 with a negative pressure source 227 through barb fitting 221. Conduit 223 communicates negative pressure suction to the heart contact member 200 through its connection with a negative pressure source at barb fitting 221. Heart manipulator 20 is manipulated by surgeon through handle 240 which extends beyond proximal open end 116 into extracorporeal space once heart manipulator is engaged in internal joint 190. Handle 240 is preferably detachable through a sliding fit between outer surface 225 and bore 245 in said handle. This sliding fit allows said handle to be positioned at a desired location along shaft member 220. When detachable handle 240 is removed from heart manipulator 20, shaft member 220 may be axially inserted into a close-ended internal joint such as 190 prior to deploying access cannula 10 into engagement with diaphragm. Alternatively, heart manipulator 20 may be transversely engaged into an open-ended internal joint such as 180, 170 even after the access cannula 10 has been engaged with the diaphragm.

Heart contacting member 200 is comprised of a substantially conical elastic sheath 204, detachably mounted to shaft member 220 through a barb fitting interface formed by mating members 202 and 222. Said sheath 204 may be produced from any suitable polymeric material approved for surgical use. Sheath 204 may be designed to have variable elastic properties by virtue of its variable thickness or by virtue of its variable composition during fabrication. Reinforcement fibers or structural ribs 201 may also be used in the fabrication of sheath 204 to bias its elasticity along certain axes. This is especially beneficial where the shaft member 220 is rigid, whereby elastic sheath 204 acts as a buffer in elastic gradient between said rigid member 220 and substantially non-rigid heart surface or non-structural membrane-like pericardium tissue if said heart manipulator is engaged with pericardium tissue. This buffer in elastic gradient may encourage the said heart surface or said pericardium tissue to remain in compliant contact with tissue-engaging perimeter 205 of said sheath.

The open area perimeter 205 is configured with a tapered and beveled terminal edge in the nature of a deformable skirt 203. This deformable skirt 203 achieves a substantially compliant seal perimeter at tissue-engaging perimeter 205, capable of engaging the surface of the heart or pericardium tissue throughout a range of spatial orientations which the said heart or said pericardium tissue may assume relative to shaft member 220. The deformable skirt 203 provides readjustment of the substantially planar surface formed by tissue-engaging perimeter 205 depending on the direction of application of tensile retraction loads applied to and reacted by the said heart or said pericardium tissue. A tensile retraction load applied to said heart or said pericardium tissue in a direction substantially parallel to the axis of shaft member 220 distorts the beveled edge of deformable skirt 203 equally around the tissue-engaging perimeter 205, in an inward direction towards the center of said tissue-engaging perimeter 205. If a tensile retraction load is applied to said heart or said pericardium tissue in a skewed direction relative to the axis of shaft member 220, the beveled edge of skirt 203 will distort unevenly around the tissue-engaging perimeter 205 in a fashion that the substantially planar surface formed by tissue-engaging perimeter 205 is now oriented substantially perpendicular to the direction of application of said manipulation force or substantially perpendicular to the heart reaction force to imposed retraction loads.

Alternatively, heart manipulator may be comprised of a plurality of conical elastic sheaths 204 configured in a manifold assembly and connected to a common hollow shaft member.

Alternatively, a heart contact member comprising a substantially conical non-flowing static suction cup made from a flexible polymeric material may be utilized.

Referring now to FIGS. 15A to 15D, a portion of a beating heart containing the apex is engaged with heart contact member 200 and is schematically represented as APX. For the purposes of illustration, the different surfaces of the beating heart are identified by four arbitrary markers: "A" marks a point on the anterior surface of the heart; "R" marks a point on the right lateral surface of the heart; "P" marks a point on the posterior surface of the heart; and "L" marks a point on the left lateral side surface of the heart. Access cannula 10 is schematically illustrated as a cylinder in end view. For the purposes of illustration, three arbitrary markers "X", "Y", "Z" are identified on the perimeter of access cannula 10. Heart manipulator 20, and more specifically heart contact member 200 is represented by its tissue-engaging perimeter 205. Internal joint 180 is reserved for coronary stabilizer 30 (not shown). Heart manipulator 20 is engaged in a similar internal joint (not shown), which for the purposes of this illustration is disposed diametrically opposite to said internal joint 180 about the centerline of access cannula 10.

Figure 9:
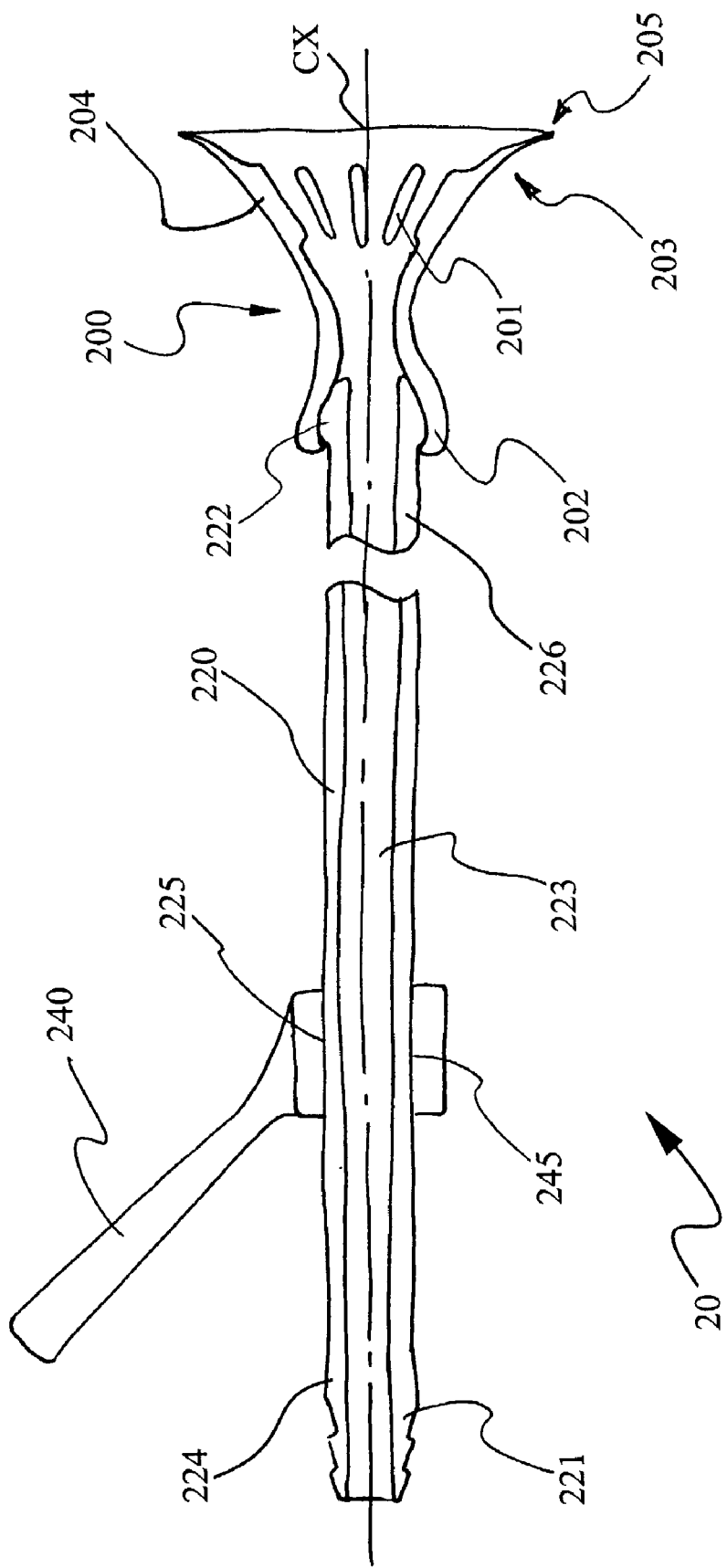
FIG. 9 is a lateral cross section view through the heart manipulator of FIG. 1.

FIG. 15A illustrates access cannula 10 secured in a desired position and orientation relative to surgical arm 50 (coarse adjustment), where internal joint 180 is located at top dead center (looking into cannula 10). When the beating heart is engaged with heart contact member 200, and the heart manipulator 20 is engaged in internal joint 180, said internal joint in its free state will allow the center of the heart contact member (labelled "CX" in FIG. 9) to be positionable anywhere within surface area AHC (area within circle labelled AHC). The size and shape of AHC is here only schematically represented as a circular area. AHC generally increases in size and its shape may vary as the distance from point CX to the center of spherical collet 182 of internal joint 180 increases. This is representative of a heart contacting member 200 being extended further into the pleural space PLS beyond the distal opening 115. Now if this variable AHC area is integrated over the range that said heart contacting member 200 is capable of extending beyond the distal opening 115, a volume results within which point CX may be positionable. The actual size and shape of AHC (and the resulting said volume) is a function of many parameters. Among these: the specific geometry of an access cannula, the number of motion degrees of freedom offered by a design of an internal joint, the range of motion of said offered motion degrees of freedom, and the distance between point CX and said internal joint. As a result of the foregoing, the apex of a beating heart when engaged with heart contacting member 200, may also be positionable within a considerable volume.

As illustrated in FIG. 15B, when access cannula 10 is re-oriented within channel clamp 510 through a 90 degree counterclockwise rotation about its centerline, surface area AHC orbits around the centerline of access cannula 10 while rotating 90 degrees counterclockwise. Nominal orbit trajectory is identified as ORB. The beating heart, represented by APX, orbits relative to the centerline of access cannula 10 but does not rotate. During this coarse readjustment, internal joint 180 is in its free state such that shaft member 220 is free to rotate about its centerline while tissue-engaging perimeter 205 remains engaged with said beating heart. By rotating access cannula 10 in the manner just described, all surfaces of the heart are generally accessible by coronary stabilizer 30 which may be deployed through the portion of hollow passageway 124 not occupied by heart manipulator 20. FIG. 15A illustrates the surgical set-up well suited to access the anterior surface of a beating heart; FIG. 15B a surgical set-up well suited to access the right lateral surface of a beating heart, FIG. 15C a surgical set-up well suited to access the posterior surface of a heart, and FIG. 15D a surgical set-up well suited to access the left lateral surface of a beating heart.

Figure 10:
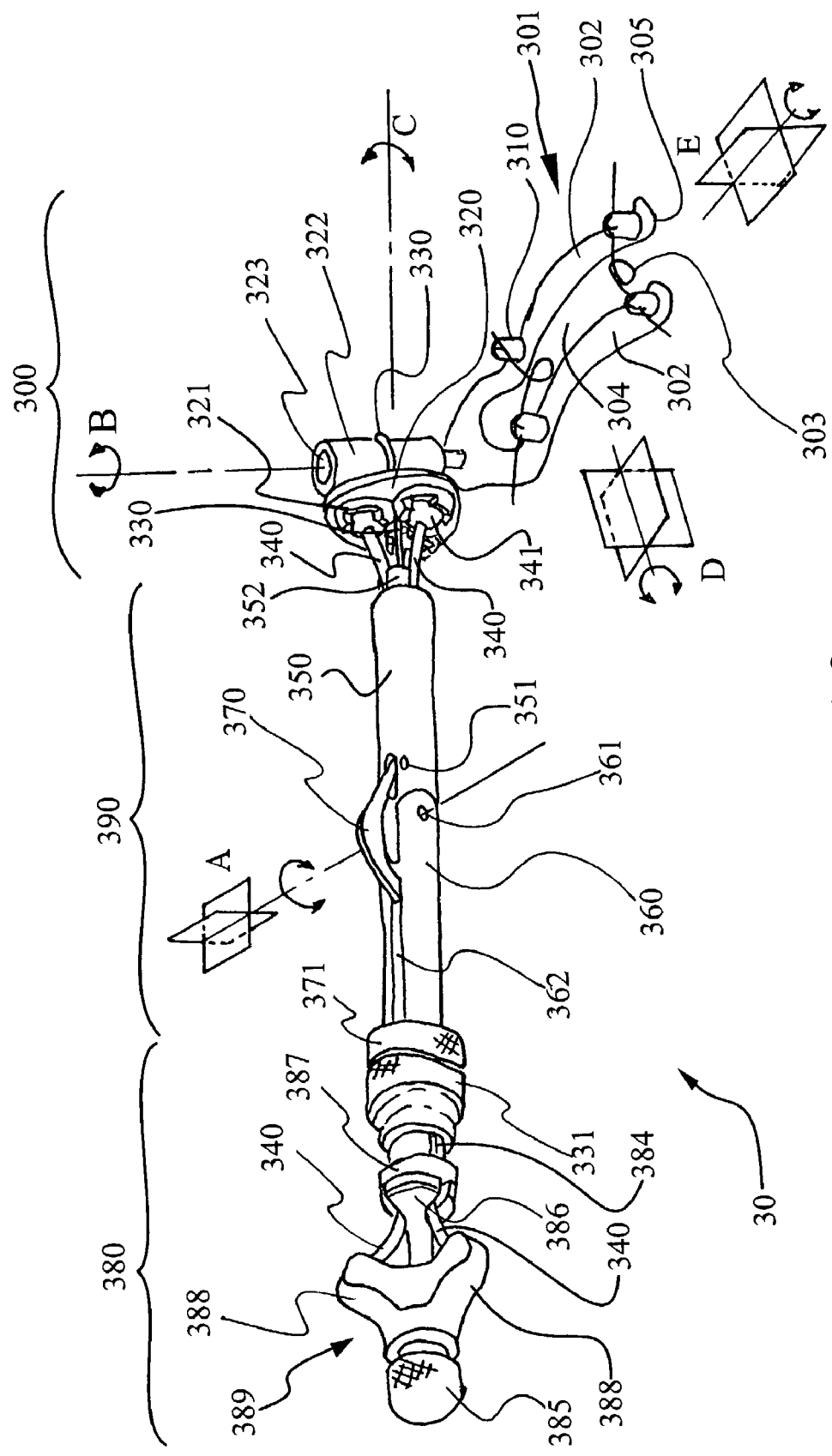
FIG. 10 is a perspective view of the coronary stabilizer of FIG. 1 illustrating the motion degrees of freedom.

Referring to FIG. 10, the coronary stabilizer 30 is comprised of three main subassemblies: a proximal extracorporeal control section 380; a distal heart-contacting section 300 deployed within the thoracic cavity; and a connector section 390 for transmitting a surgeon input from said control section to said heart-contacting section.

The control section 380 comprises a securing bolt 385, a multi-socket cradle 389, an annular brace 387, an first adjustment dial 371, and a second adjustment dial 331. Cradle 389 is configured with three lobes 388, only two of which are visible in FIG. 10. Each lobe 388 is configured with a spherical socket (not shown) that engages a spherical end (not shown) disposed on each of the three articulation transmission cables 340. Said spherical ends may be permanently engaged with said spherical sockets in cradle 389 by flaring the socket perimeter around the spherical end. Alternatively, said spherical ends may be demountably engaged with said spherical sockets by virtue of a "snap in" design. Inner rod 386 is configured with three longitudinal channels 384 that each serve to house one of the transmission cables 340.

The cradle 389 is also configured with a central spherical socket (not shown) to engage and cooperate with a substantially spherical end (not shown) on the proximal extremity of inner rod 386. The perimeter which defines the opening of said central spherical socket is locally flared a three locations to create a perimeter with three flared edges. Said substantially spherical end of inner rod 386 is configured with three flats that allow it to be insertable past the said three flared edges of central spherical socket in cradle 389. Cradle 389 is subsequently rotated with respect to centerline of inner rod 386, such that said flared edges on central spherical socket engage with a portion of the spherical end of rod 386 not interrupted by said flats. This results in cradle 389 and inner rod 386 being movably connected while being pivotingly engaged. This orientation of cradle 389 relative to inner rod 386 is maintained when the spherical ends of each of the three transmission cables 340 are engaged with the spherical sockets in lobes 388 while said cables are located in channel 384.

The center socket in cradle 389 is pierced by a threaded hole (not shown), at its topmost point, to cooperate with securing bolt 385. Applying a torque on said bolt results in a force being exerted on the spherical end of rod 386, thereby securing said spherical end against the three flared edges of cradle 389. This results in a locked assembly. Loosening bolt 385 permits sliding at the spherical interface between spherical end of rod 386 and central socket of cradle 389.

Transmission cables 340 extend from a control section 380 to a heart-contacting section 300 through a connector section 390. Said transmission cables slide in a substantially closed passage formed by longitudinal channel 384 and the inner diameter of hollow proximal shaft 360. Said transmission cables 340 slide in a similar substantially closed passage formed by a longitudinal channel (not shown) in distal inner rod 352 and inner diameter of hollow distal shaft 350. By pivoting the cradle 389 relative to spherical end of rod 386, each of the articulation transmission cables 340 will slide within its respective closed passage, a variable and different amount based on the relative orientation of cradle 389 relative to inner rod 386. By virtue of its connection with each of the transmission cables 340, this variable and different amount of sliding experienced by each of the three cables will allow plate member 320 to assume a multitude of different spatial orientations. An annular brace 387 is inserted over inner rod 386 serving to retain cables 340 within their longitudinal channel 384 at the proximal control section 380. A similar brace may also be installed at the distal heart-contacting section 300.

Each of the transmission cables 340 is configured with a distal spherical end 341. Each of said spherical end 341 is engaged to a quick assembly/disassembly interface socket 321 on plate member 320, thereby serving to connect heart-contacting section 300 with connector section 390.

Heart-contacting section 300 is comprised of at least one contact member 301, a shaft member 323, a plate member 320, and a bushing 322. Contact member 301 is configured by two elongated contact arms 302 defining therebetween an arterial window 304. Two arms 302 are preferably substantially parallel and configure a substantially planar contact surface. Two contact arms 302 may be provided with a textured underside surface 305 to improve adherence with the surface of a beating heart when placed in contact with said heart.

Contact member 301 serves to immobilize a portion of the surface of the beating heart proximate to a target coronary artery that will require a surgical intervention, such as an anastomosis. Contact arms 302 are shaped to be capable to press against the surface of a beating heart. Said arms are positioned on the said surface of a beating heart in such a manner as to straddle the target coronary artery proximate to the arteriotomy site within the arterial window 304. Contact member 301 is rigidly connected to shaft member 323. Bushing member 322 is rigidly connected to plate member 320 on opposite side of sockets 321. Shaft member 323 is rotatingly engaged with bushing member 322.

Axis B is the longitudinal axis of rotation of shaft member 323. Axis E is parallel to the plane containing plate member 320 and is normal to Axis B. Axis D is the longitudinal axis of distal shaft 350. Axis D substantially intersects Axes B and E.

The substantially planar contact surface of contact member 301 may be positioned and oriented with respect to distal shaft 350 through plate member 320 which is in turn positioned and oriented through its connection with transmission cables 340 which respond to a surgeon input applied at cradle 389. This results in two motion degrees of freedom. The first motion degree of freedom is a rotation about Axis E which causes contact member 301 to tilt relative to distal shaft member 350. The second motion degree of freedom is a rotation about Axis B which causes contact member 301 to yaw relative to distal shaft member 350.

The coronary stabilizer 30 may also be provided with an additional adjustment that allows distal shaft member 350 to pivot relative to proximal shaft member 360 about Axis A. Axis A is the centerline through hinge 361. This additional adjustment allows the heart contacting member 301 to be set in a position and orientation substantially offset from the longitudinal axis of access cannula 10, when said contact member 301 extends distally beyond the distal open end 115 of said access cannula. This additional adjustment is especially useful in adjusting the orientation and position of the contact member 301 relative to access cannula 10, in a manner that tends to improve the presentation of said contact member on the target arteries located on the wider portions of a beating heart. This improved presentation of contact member 301 on the surface of the beating heart proximate to the target coronary artery also tends to improve the efficacy of the subsequent imposed immobilization by said contact member. The rotation of dial 371 entrains through its engagement with a sliding member (not shown) within the proximal shaft 360 the translation of elbow 370 within slot 362. As a result, shaft 350 pivots about hinge 361 to a desired angle. The eccentricity of distal hinge 351 with respect to proximal hinge 361 results in a bias direction of pivot when a torque is applied to adjustment dial 371. This results in a fourth motion degree of freedom namely pivoting about Axis A which is coincident with centerline of hinge 361.

Inner rod 386 is rotatingly engaged with proximal shaft 360 along its longitudinal Axis C. Inner rod 352 is rotatingly engaged with distal shaft 350. Rotating cradle 389 relative to proximal shaft 360 about axis C entrains a rotation of plate member 320 by virtue of the simultaneous engagement of cables 340 with the sockets in lobes 388 of cradle 389, the longitudinal channels 384 in inner rod 386, and the interface sockets 321 in plate member 321. This results in a fourth motion degree of freedom namely, rotation about axis D which allows contact member 301 to revolve about said axis relative to distal shaft member 350.

Coronary stabilizer 30 may also be provided with an additional adjustment enabling the rotation of contact member 301 about Axis B. This allows the angular orientation of the arterial window 304 with respect to shaft 350, in order to more adequately access target arteries that are disposed in a diagonal orientation with respect to the long axis of the heart. Rotation of dial 331 acts on a fourth return transmission cable 330, which in turn applies a torque on shaft 323 attached to contacting member 301. Shaft 323 rotates within bushing 322. This results in an increased range for the second motion degree of freedom, that is, rotation about axis B.

Coronary stabilizer 30 tends to react mostly the local forces exerted by the underlying pulsating myocardium that it immobilizes. The loads associated with positioning and orienting the entire beating heart within the thoracic cavity are reacted mostly by the heart manipulator 20.

To achieve a substantially bloodless surgical field during beating a heart bypass surgery, heart contacting member 301 is configured with at least one wire attachment pedestal 310. As illustrated in FIG. 10, four such pedestals 310 are provided, two pedestal 310 on each of contact arms 302 disposed on opposite sides of arterial window 304. Said pedestals 310 serve to engage a vessel occluding wire 303, preferably a silicone elastomer vascular loop. One said wire circumvents the target artery upstream of the grafting site while the other circumvents the target artery downstream of the grafting site. The two loose ends of each said wire 303 are subsequently engaged in opposing pedestals 310 located on opposite contact arms 302. As such, the target artery is substantially snared by the deployment of said wire 303 tending to occlude said artery and create a substantially bloodless surgical field. The said pedestals 310 are each provided with at least one slit which tends to achieve a light-tight anchoring of vessel occluding wire 303. Light-tight anchoring will retain said wire 303 engaged with said slit in pedestal 310 up until a threshold tension is applied to the occluding wire 303. At this point, said wire will begin to slip through said slit. This tends to favor non-traumatic disengagement of said wire from said slit in the eventuality of an unwanted slippage of the coronary stabilizer 30 or an undesirable movement of the beating heart. Said slits in pedestals 310 allow a surgical wire 303 in the nature of a silicone elastomer vascular loop engaged therein to be pulled through said slit from a first engaged position to a second engaged position without having to disengage said wire from said slit.

When proximal shaft member 360 of coronary stabilizer 30 is engaged in internal joint 190 (or like joint 180), said internal joint in its free state will provide four motion degrees of freedom. That is: translation of proximal shaft member 360 along centerline of bore 195, rotation of proximal shaft member 360 about centerline of bore 195, pivoting of proximal shaft member 360 about centerline through bore 192, pivoting of proximal shaft member 360 about an axis perpendicular to centerline through bore 192 and simultaneously perpendicular to centerline of bore 195. In addition, when internal joint 190 (or 180) is in its free state, four additional motion degrees of freedom about axes A, B, D and E are provided by virtue of the design of coronary stabilizer 30. When internal joint 190 (or 180) is in its locked state the motion degrees of freedom offered by internal joint 190 (or 180) become locked. However, the four additional degrees of motion offered by the design of the coronary stabilizer 30 may still be exploited through a surgeon input applied at either cradle 389, dial 331, dial 371 or any combination thereof. A surgeon input applied at proximal control section 380 results in a linked corresponding movement of heart contact section 300 within the internal body cavity and downstream of anatomic barrier. As such, this provides an additional level of adjustment which may be exploited to tend to optimize the presentation of coronary stabilizer 30 upon the beating heart in addition to the "fine adjustment" and "coarse adjustment". This additional level of adjustment also provides a means for readjusting the contact pressures exerted by the coronary stabilizer during a surgical procedure, without having to disrupt the "fine" and "coarse adjustments".

The design concepts described in reference to coronary stabilizer 30 may also be applied to a heart manipulator 20, especially if heart contacting member 200 is a non-flowing static suction cup. As such, the heart contacting member 200 may be further deployed in space relative to the distal end 226 of shaft member 220.

Figure 11A:
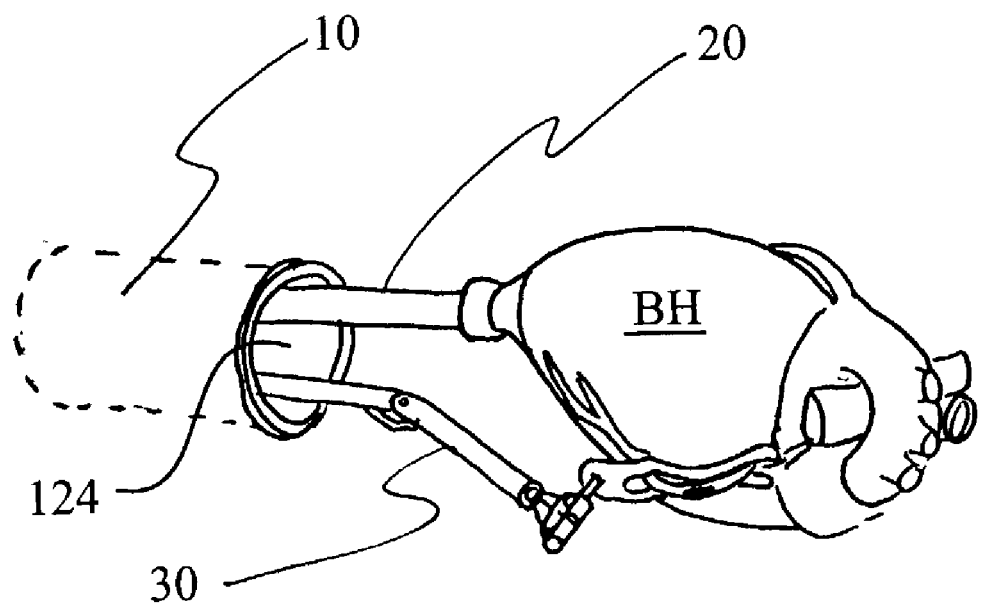
FIGS. 11A and 11B illustrate the cooperation of the access cannula, the heart manipulator and the coronary stabilizer of FIG. 1 in gaining access to the different coronary territories.
Figure 11B:
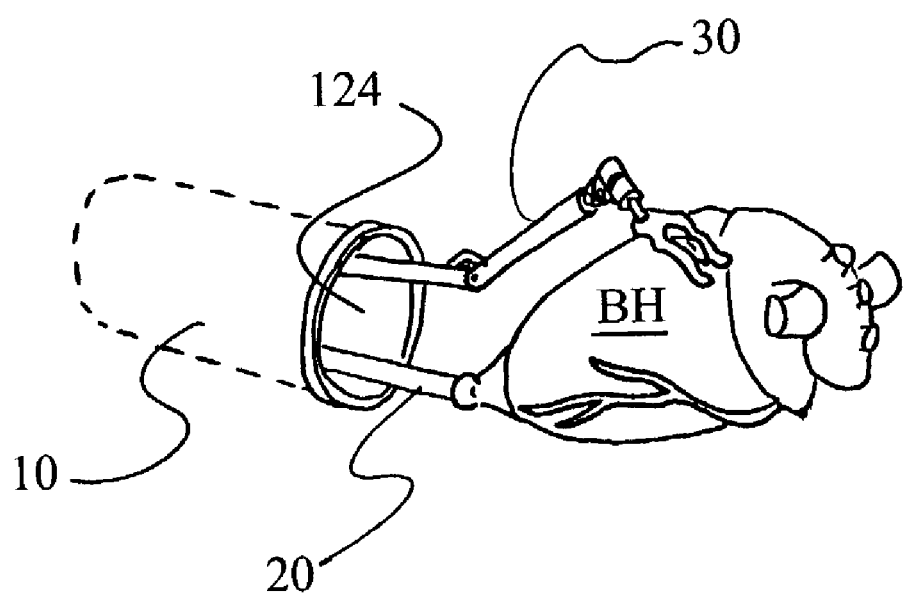

Referring to FIGS. 7, 11A and 11B, heart manipulator 20 and coronary stabilizer 30 are illustrated engaged with access cannula 10 and with a beating heart. Handle 240 and control section 380 extend beyond proximal opening 116 into the extracorporeal space ECS. Heart contacting member 200 and heart-contacting section 300 extend into the pleural space PLS beyond the diaphragm DG and downstream of open end 115. Heart contacting member 200 and heart-contacting section 300 are engaged with target internal cardiac tissue, more specifically a portion of a beating heart surface. FIG. 11A illustrates a beating heart oriented and positioned relative to access cannula 10 by heart manipulator 20 so that coronary stabilizer 30 may access the posterior surface of the heart. FIG. 11B illustrates a beating heart oriented and positioned relative to access cannula 10 by heart manipulator 20 so that coronary stabilizer 30 may access the anterior surface of the heart.

Figure 17B:
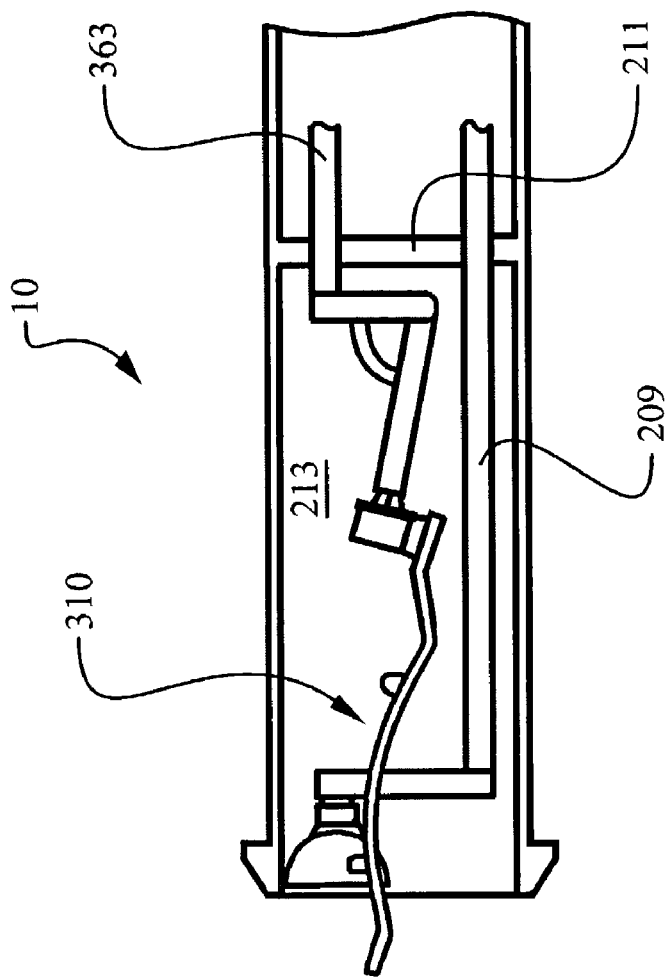
FIGS. 17A to 17D illustrate the range of motion available to a variant of a heart manipulator engaged with an access cannula according to an aspect of the present invention.
Figure 17A:
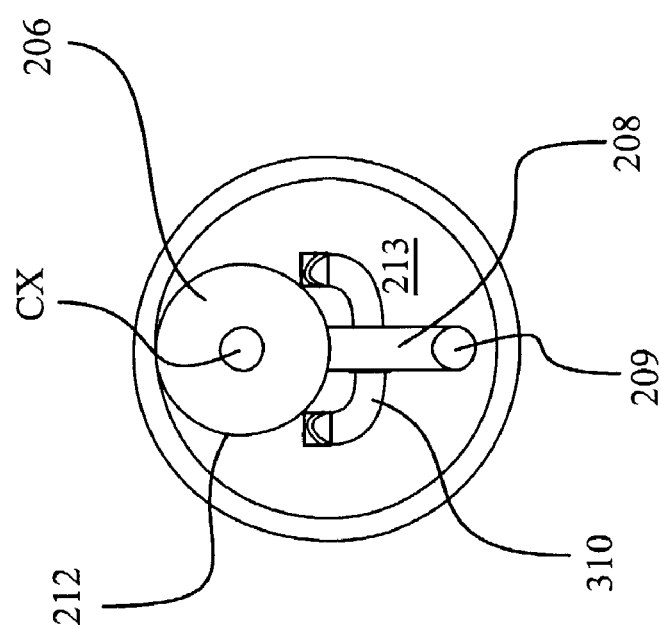

FIGS. 17A-17D illustrate a variant to the first embodiment according to the present invention. Coronary stabilizer 31 and heart manipulator 21 are substantially fully enclosed within the at least one hollow passageway 213 of access cannula 10, in an initial retracted state (FIGS. 17A, 17B). Hollow shaft 363 of coronary stabilizer 31 is engaged with an internal joint (not shown) within hollow passageway 213, located upstream of seal member 211. Coronary stabilizer 31 is comprised of a substantially fixed joint 364 between hollow shafts 363 and 366, and a pivoting joint 365 between hollow shafts 366 and 367. Longitudinal axes of shafts 363 is substantially parallel to longitudinal axis of access cannula 10. Shaft 366 is substantially perpendicular to shafts 363.

Contact member 310 is engaged with distal end of hollow shaft 367. At least three articulation cables (not shown) extend through each of hollow shafts 367, 366, 363 and serve to position and orient contact member 310 relative to shaft 367 in a similar manner to the first embodiment. In addition, contact member 310 may also revolve around the longitudinal axis of shaft 367 by virtue of a torsional cable also disposed along hollow shafts 367, 366, 363. A proximal control section similar to 380 of the first embodiment is also provided (not shown) to tranfer the surgeon input to the heart contacting member 310.

Hollow shaft 209 of heart manipulator 21 is engaged with an internal joint (not shown) within hollow passageway 213, located upstream of seal member 211. Heart manipulator 21 is comprised of two hollow shafts 209, 208 connected through a substantially rigid joint 210 in a substantially perpendicular orientation. The centerline of shaft 209 is substantially parallel with the longitudinal axis of access cannula 10. Heart contact member 250 is comprised of an elastic conical sheath 206 which is rotatingly engaged with shaft 208 through rotatable pneumatic joint 207. Tissue-engaging perimeter 212 engages with the surface of the beating heart in a similar fashion to the first embodiment.

Said joint 207 is rotatable in order to provide torsion free displacements to a beating heart which is engaged through sheath 206.

In the retracted state, hollow shaft 208 of heart manipulator 21 rests between the contact arms of contact member 310. Access cannula 10 is preferably cylindrical and shafts 363, 209 are preferably diametrically opposed relative to the centerline of access cannula 10. This tends to minimize the overall dimensions of access cannula 10 needed to fully enclose coronary stabilizer 31 and heart manipulator 21 in the retracted state within hollow passageway 213.

Heart manipulator 21 is deployed before coronary stabilizer 31. Heart manipulator 21 is extended into the thoracic cavity sufficiently to be able to rotate freely about the centerline of shaft 209 without interfering with contact arms of retracted coronary stabilizer 31. Heart manipulator 21 may extend further into thoracic cavity until it is capable of coming into contact with the target internal cardiac tissue, preferably the apex of the beating heart. The rotation of heart contact member 250 about the centerline of shaft 209 is a "fine adjustment" motion degree of freedom enabled by the internal joint. Said internal joint secures the position and orientation of heart manipulator 21 relative to access cannula 10.

When access cannula 10 is secured in a desired position and orientation relative to surgical arm 50 (coarse adjustment), and when the internal joint engaged with shaft 209 of heart manipulator 21 is in its free state, center CX of heart contact member 250 is free to assume any position along circumference CHC, for a given distance between point CX and center of said internal joint. As such, heart contact member 250 orbits around the centerline of shaft 209. If sheath 206 is engaged with the surface of a beating heart, then said sheath 206 also rotates about point CX as it orbits, by virtue of rotatable joint 207.

When access cannula 10 is re-oriented within channel clamp 510, thereby rotating about its centerline axis, circumference CHC orbits about the centerline of access cannula 10 along a trajectory ORB. If the apex of a beating heart is engaged with sheath 206 during this re-orientation of access cannula 10, then the apex will also orbit about the centerline of access cannula 10 but will not rotate. By rotating access cannula 10 in the manner just described, all surfaces of the heart are generally accessible by coronary stabilizer 31 which is independently deployed relative to heart manipulator 21.

Figures 17C, 17D:
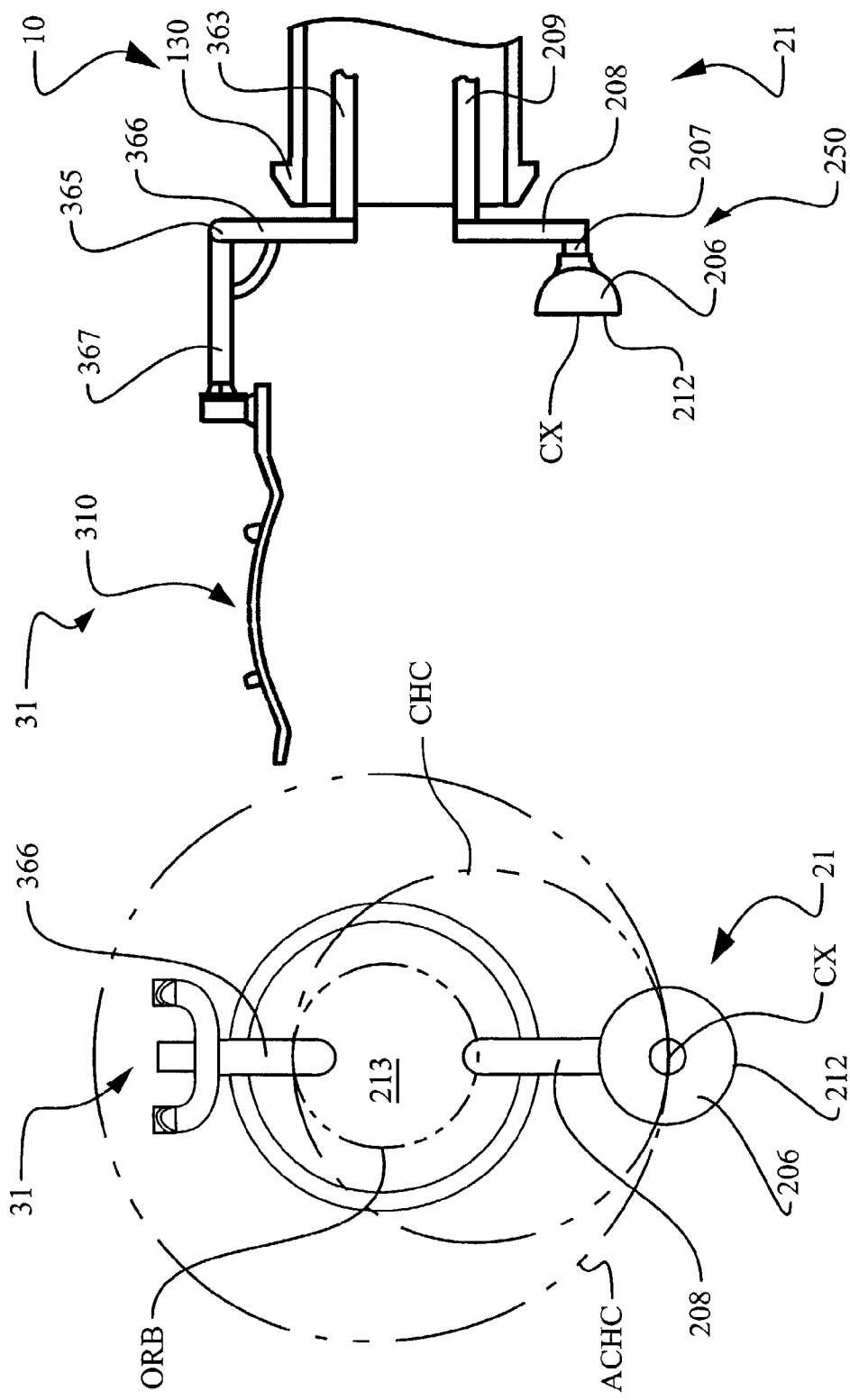
Figure 18A:
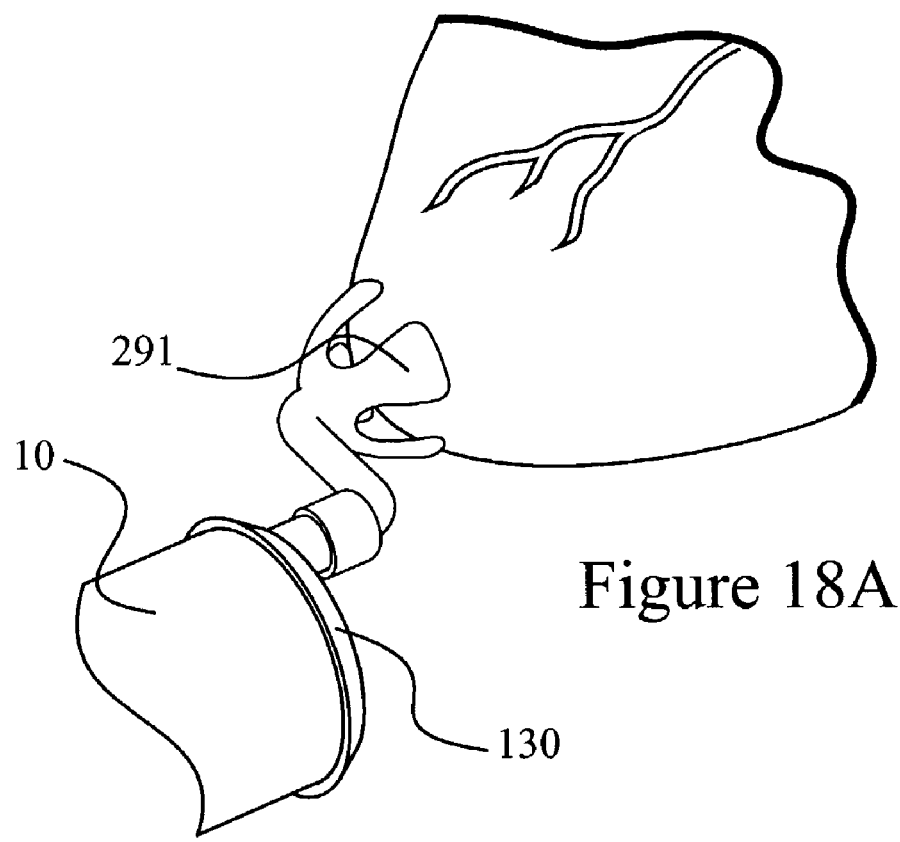
FIGS. 18A and 18B illustrate variants of a heart contacting member of the heart manipulator of FIG. 1.
Figure 18B:
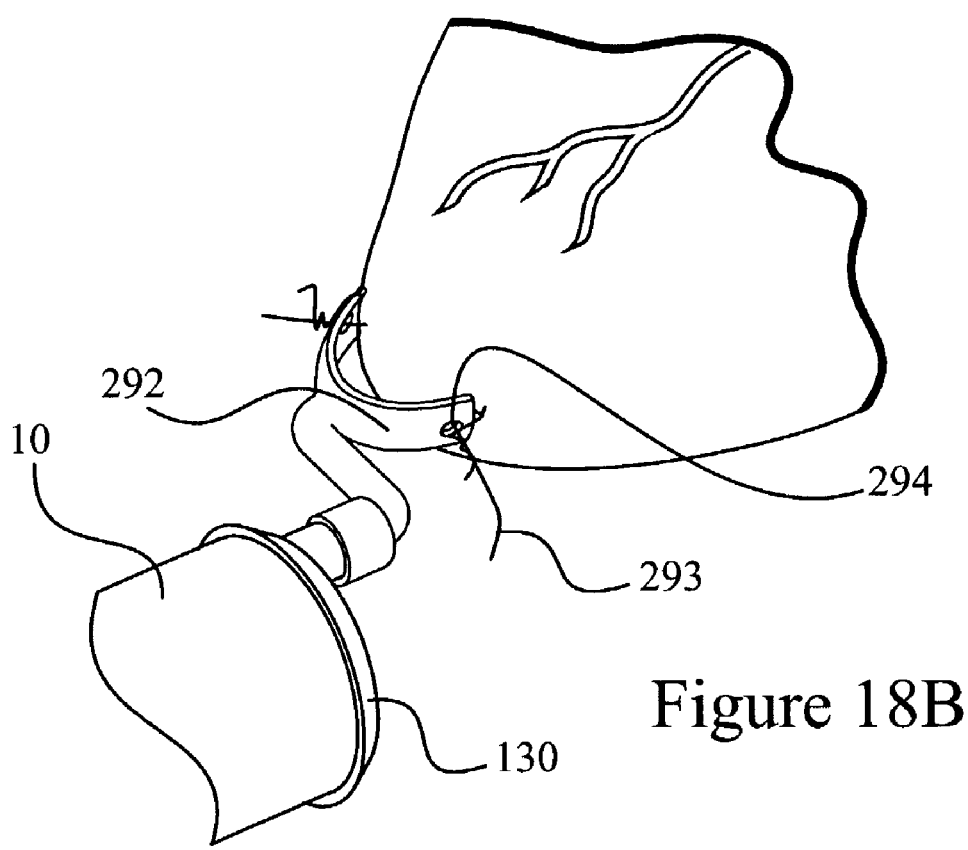
Figure 19:
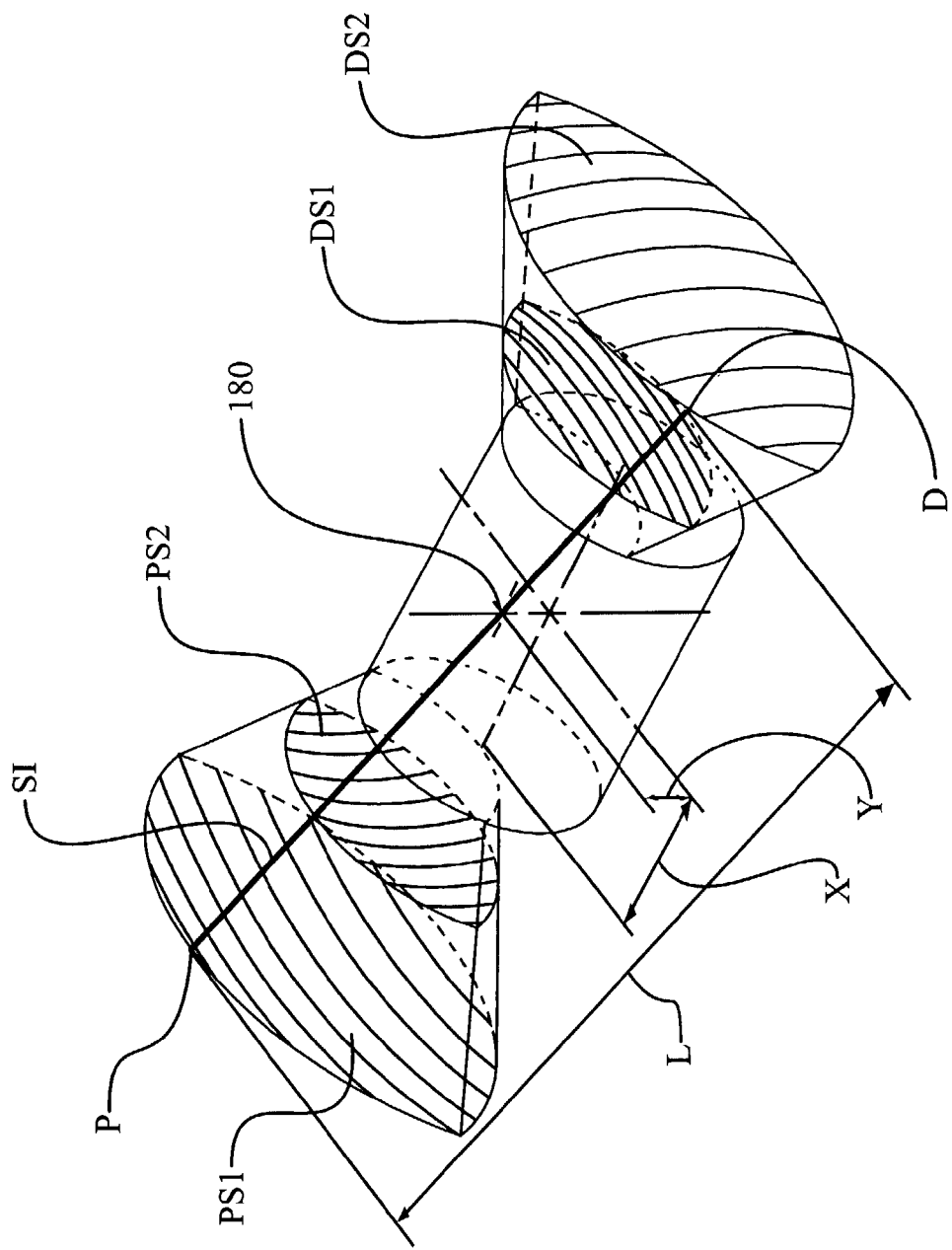
FIG. 19 is a schematic representation of the range of motion afforded to a surgical instrument within an access cannula according to the present invention.

Referring to FIG. 17C, almost any point within the area ACHC may be engaged by sheath 206 through the combination of a rotation of heart contact member 250 about the centerline of shaft 209 (fine adjustment) and a rotation of access cannula 10 about its centerline (coarse adjustment). Once engaged, this point may be subsequently positioned and oriented relative to access cannula 10 by a combination of coarse and fine adjustments FIGS. 18A and 18B illustrate variants in heart contacting member 250. FIG. 18A illustrates a heart contacting member comprising a plurality of substantially rigid finger-like protrusions 291. FIG. 18B illustrates a heart contacting member comprising a substantially hemi-cylindrical cradle 292 with perforations 294 to allow anchoring preferably to the apex tissue of a beating heart with an associated suture 293.

By way of a general overview, FIG. 20 illustrates a surgical apparatus 2 according to a second embodiment of the present invention. The surgical apparatus 2 is comprised of a surgical arm 50, an access cannula 10, a heart manipulator 20, a coronary stabilizer 30, and a variety of endoscopic instruments 90. Endoscopic instruments 90 represent a variety of surgical instruments well-suited to perform a surgical intervention on a beating heart while deployed through access cannula 10. At least a portion of each of the surgical instruments comprising endoscopic instruments 90 is able to engage access cannula 10 through an internal joint such as internal joint 180. Some of the surgical instruments comprising endoscopic instruments 90 may also be deployed through access cannula 10 during a part of a surgical procedure without being engaged in said internal joint 180. Endoscopic instruments 90 are generally deployed while heart manipulator 20 is engaged with a beating heart and while heart manipulator 20 is securing a desired position and orientation of said beating heart with the aim of facilitating the surgical procedure performed by endoscopic instruments 90. In other instances, endoscopic instruments 90 may be deployed while both heart manipulator 20 and coronary stabilizer 30 are engaged with a beating heart. Endoscopic instruments 90 may be comprised of some conventional endoscopic instruments capable of being engaged within said internal joint 180.

Figure 22A:
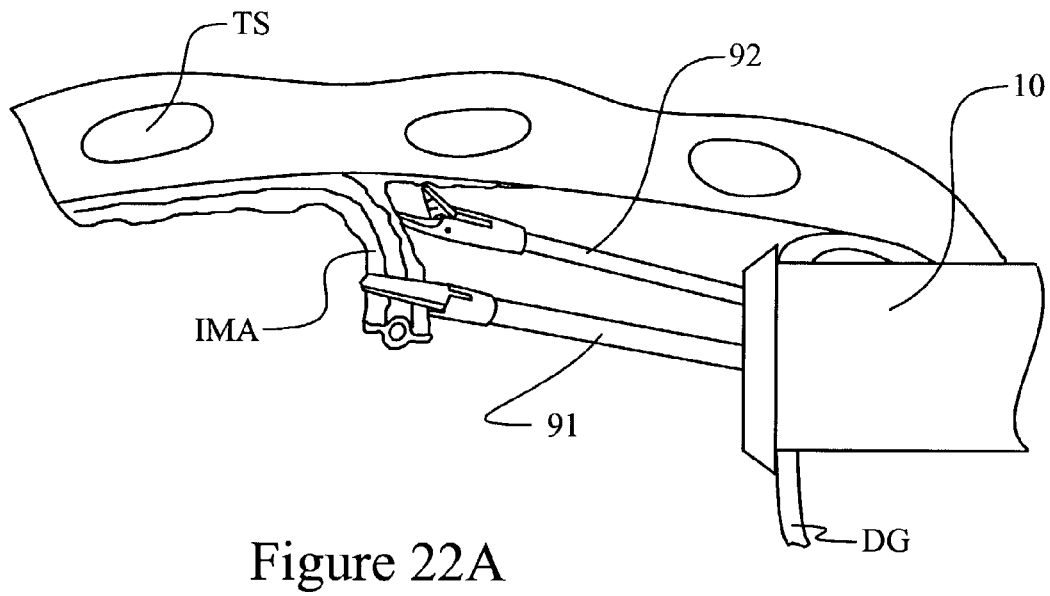
FIGS. 22A to 22G illustrates a variety of endoscopic surgical instruments engaged with an access cannula and performing a variety of surgical procedures on a beating heart according to an aspect of the present invention.

FIG. 22A illustrates a surgical method of harvesting an internal mammary artery IMA by using endoscopic instruments which are engaged with access cannula 10. Endoscopic scissors 92 are used to section internal mammary artery IMA from the internal wall of the thoracic cavity, while endoscopic forceps 91 hold and suitably position the internal mammary artery. Alternatively, endoscopic scissors 92 may be replaced by a scalpel, a cauterizing scalpel, an ultrasonic scalpel, or other like means.

Figure 22B:
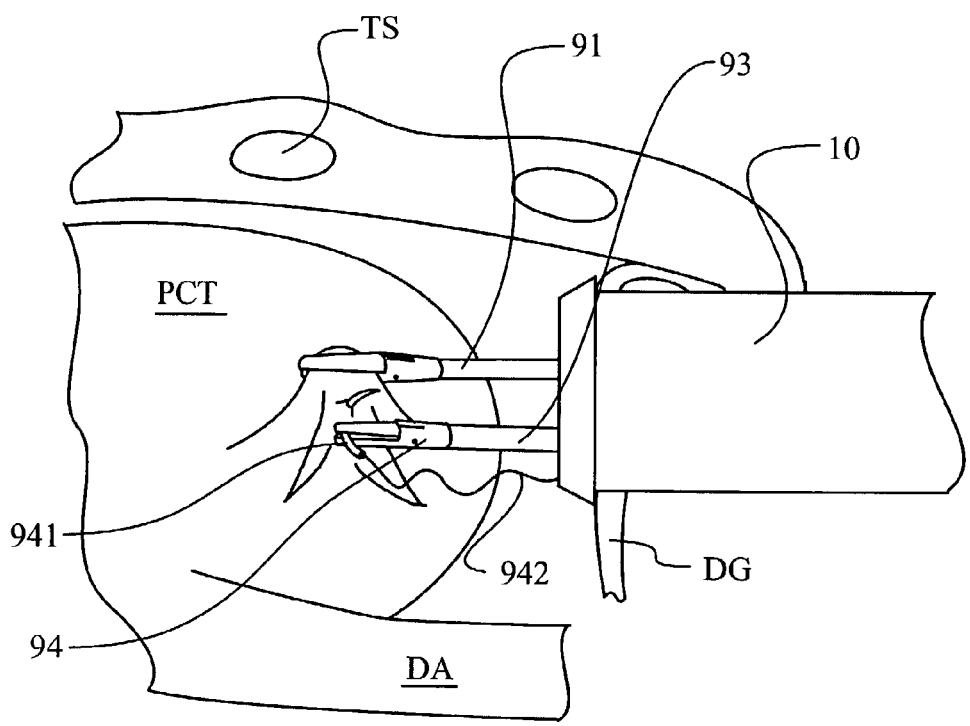

FIG. 22B illustrates a surgical method for deploying a pericardial traction suture 94 through the use of endoscopic instruments 90. Endoscopic forceps 91 pinch pericardium tissue PCT while endoscopic needle holder 93 simultaneously pierces the pericardial tissue with needle 941.

Figure 22C:
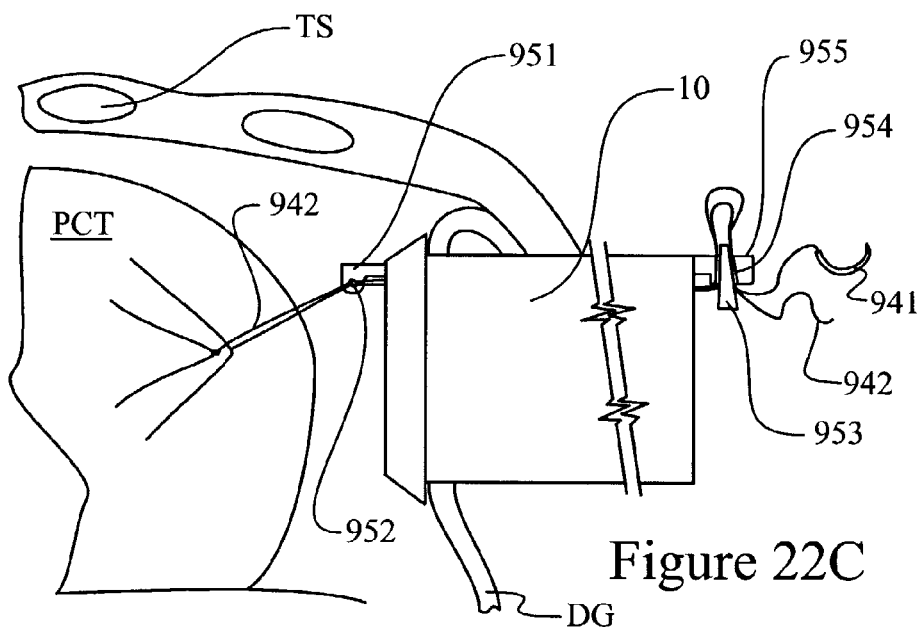

FIG. 22C illustrates a surgical method of securing a pericardial traction load by engaging traction suture 942. A pericardial traction suture 942 is first engaged through an aperture 952 disposed on a member 951, which extends distally away from the distal end of access cannula 10 into the pleural space. Subsequently, said suture 942 is anchored into an anchoring port 955. Suture 942 is anchored by virtue of a wedging action produced when plug 953 is inserted into aperture 954 thereby trapping said suture 942.

Figure 22D:
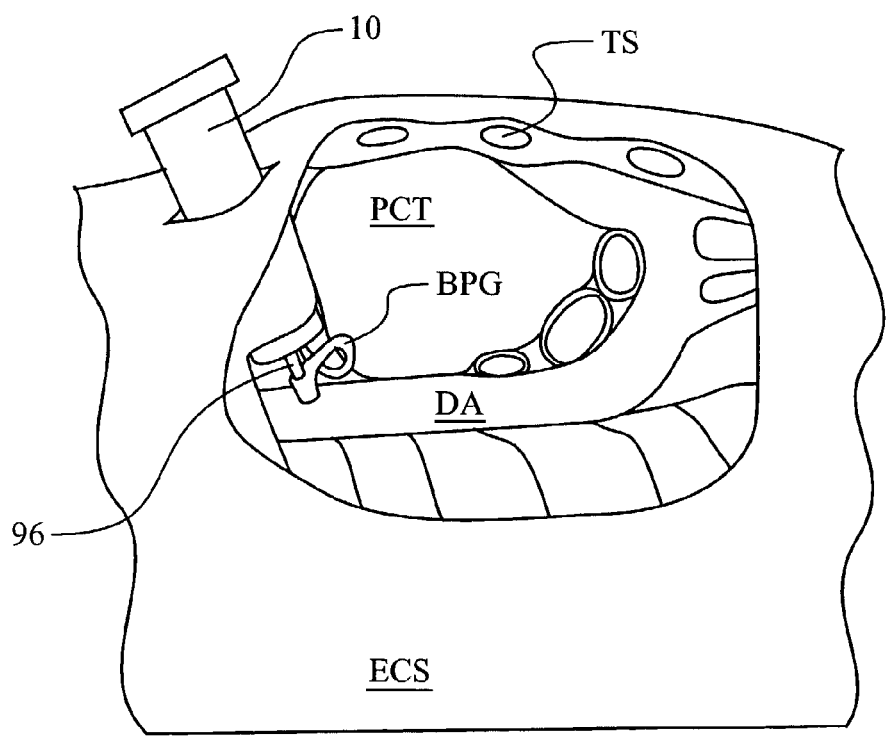

FIG. 22D illustrates a surgical method of performing a proximal anastomosis of bypass graft BPG onto descending aorta DA. The method illustrated comprises the use of a shape memory alloy stent to anchor bypass graft BPG to descending aorta DA. Bypass graft BPG may be engaged with said stent extracorporeally prior to introducing said bypass graft into the thoracic cavity. Alternatively, a side biting clamp can engage a portion of descending aorta DA thus isolating a part thereof and the bypass graft can be sutured onto the aorta after opening a suitably sized hole in the isolated portion of the aorta.

Figure 22E:
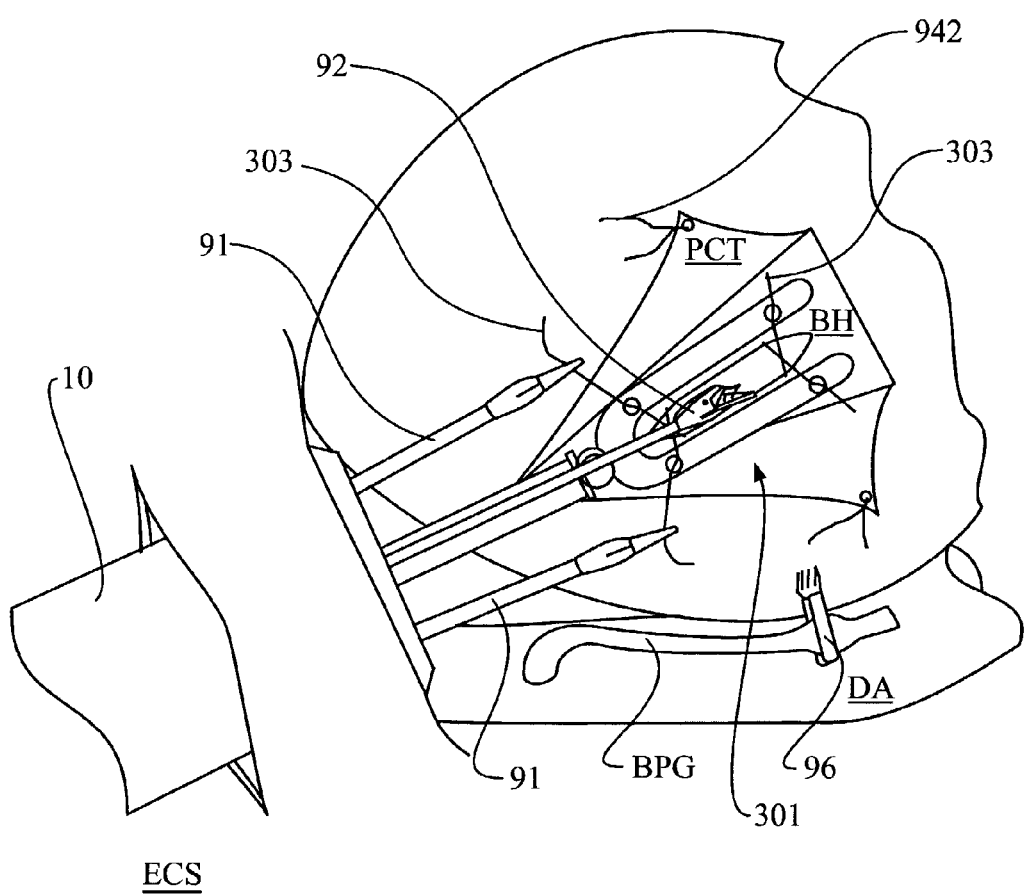

FIG. 22E illustrates a surgical method of performing an arteriotomy incision in a target artery. The target artery is occluded by engaging occluding wires 303 in pedestals 310, and applying sufficient tension to occluding wire such that snaring occurs. Endoscopic scissors 92 engage the target artery to excise a portion thereof while beating heart BH is locally immobilized by engaging contact member 301 of coronary stabilizer 30 with the heart surface proximate to the target artery. Bulldog clamp 96 engages bypass graft BPG to occlude blood flow from the descending aorta. Occluding wires 303 are engaged with the target artery by using forceps 91. Forceps 91 and scissors 92 are deployed through access cannula 10.

Figure 22F:
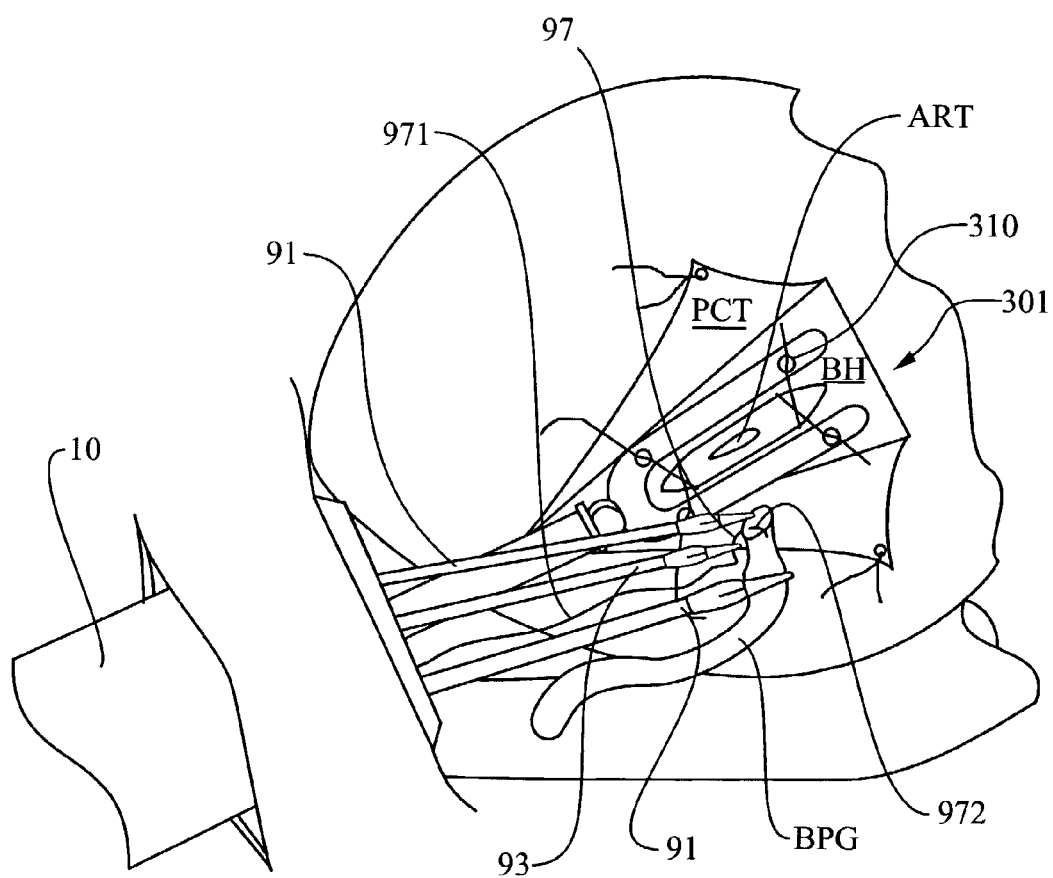

FIG. 22F illustrates a surgical method for performing of a distal anastomosis to a target coronary artery. Two forceps 91 engage and immobilize bypass graft BPG while endoscopic needle holder 93 engages suture 97 with bypass graft BPG. The proximal forceps 91 also function to occlude the bypass graft and thus prevent bleeding through the patent graft during surgery.

Figure 22G:
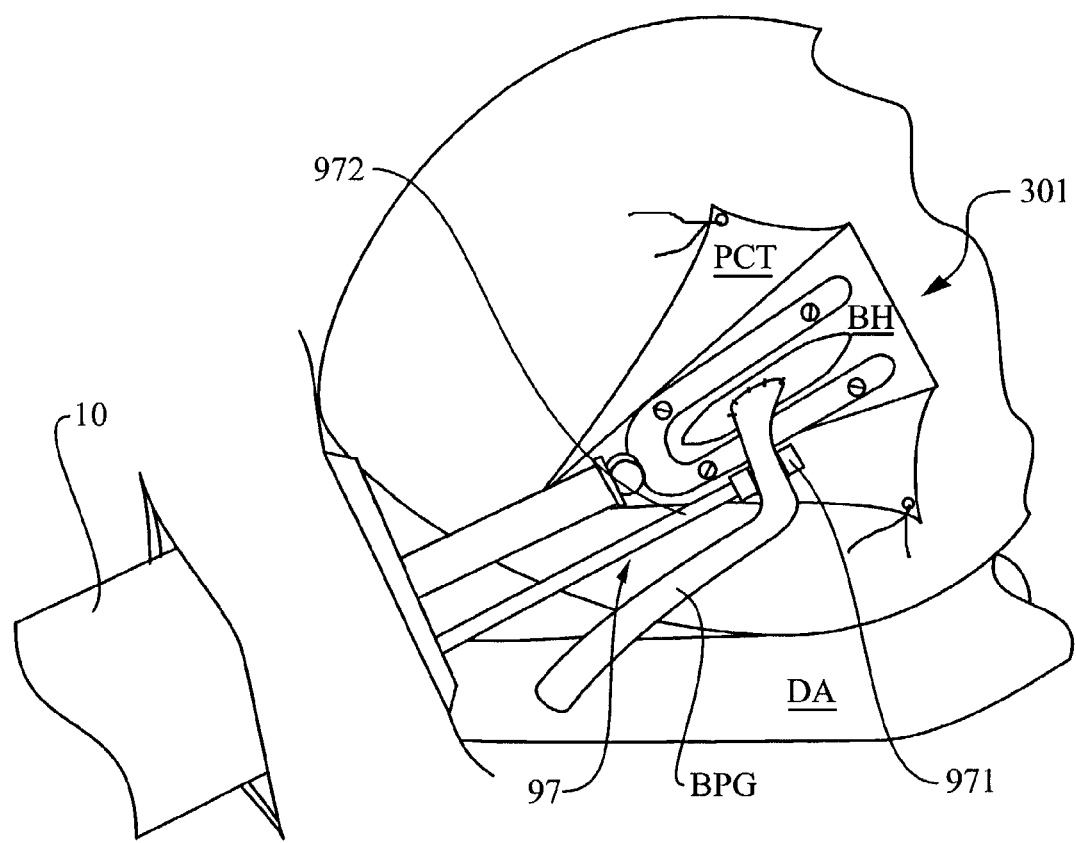

FIG. 22G illustrates a surgical method of performing doppler ultrasonography with an endoscopic ultrasonic doppler probe 971 engaged with bypass graft BPG.

Figure 21A:
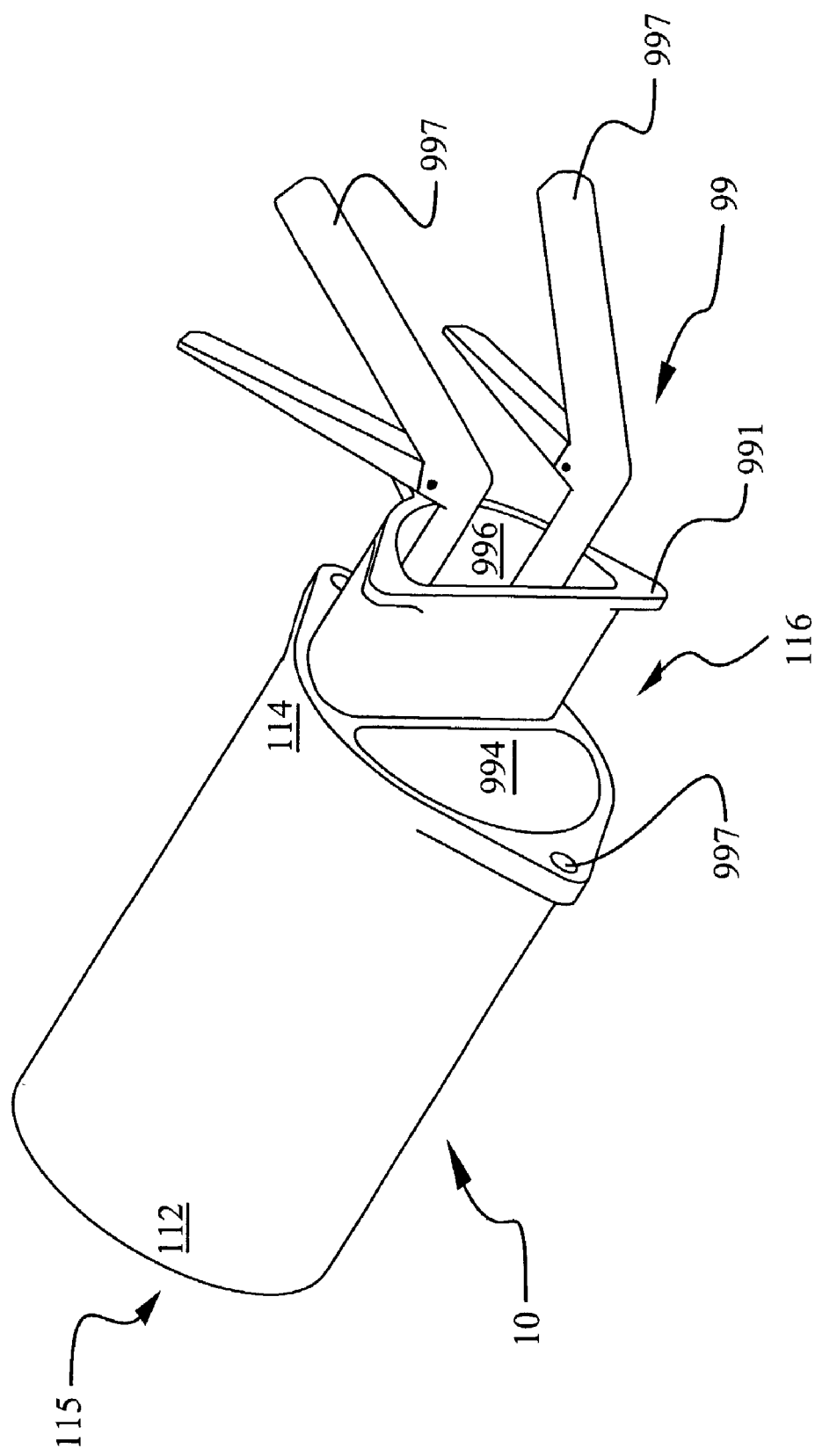

Referring to FIGS. 21A-21C, a hollow passageway 995 of an access cannula 10 may be reserved for engagement with a cartridge 99. Cartridge 99 is configured with at least one hollow passageway 996 which extends from a proximal open end to a distal open end. At least one surgical instrument, such as a forcep 91, is preferably permanently engaged within an internal joint disposed within said hollow passageway 996. An internal joint such as 180 or 150 is preferable, although other internal joints with fewer motion degrees of freedom may also be used. Hollow passageway 996 may be provided with a seal member 70 (not shown) in order to preserve the ambient conditions present within the internal body cavity. A seal member 993 may also be provided within hollow passageway 995 of access cannula 10 in order to preserve the ambient conditions present within the internal body cavity during changeover of cartridges or when no cartridge is engaged with said hollow passageway 995. Seal member 993 is displaced by cartridge 99 during installation of said cartridge into passageway 995 as illustrated in FIG. 21C. As such, during the installation and removal of cartridge 99 there is always at least one seal member, 993 or 70, acting to seal hollow passageway 995. When cartridge 99 is fully assembled into access cannula 10, distal end 998 of representative surgical instrument 91 extends distally beyond distal open end 115 of said access cannula 10, and proximal end 997 extends proximally beyond proximal open end 116 of said access cannula 10. A handle member in the nature of a flange 991 is also provided serving to limit the amount of insertion of said cartridge 99 into said passageway 995, and also serving to extract said cartridge 99 from access cannula 10. Feature 992 on cartridge 99 and feature 997 on access cannula 10 cooperate to provide a locking means between said cartridge and said access cannula. For instance, a quarter turn fastener, a detented pin, a screw, a wire, or other like means may be used. Alternatively, locking may be provided by virtue of a snug fit between cartridge 99 and access cannula 10.

A variety of cartridges may be assembled, wherein each cartridge is comprised of a different surgical instrument. Each different cartridge is intended for a different surgical procedure. Used in this manner, cartridges may facilitate or accelerate the substitution of a surgical instrument engaged in a hollow passageway of access cannula 10 by a different surgical instrument to be used in a subsequent surgical intervention. A cartridge may also serve to bundle two or more different surgical instruments (or two or more similar surgical instruments), which are used in conjunction to perform a particular surgical intervention. This allows a rapid changeover in surgical set-up from a first surgical intervention to a subsequent different surgical intervention. For instance, a cartridge bundling surgical instruments for performing harvesting of an internal mammary artery may be rapidly disengaged from access cannula 10 and replaced with a cartridge bundling surgical instruments for performing a distal anastomosis.

Figure 12:
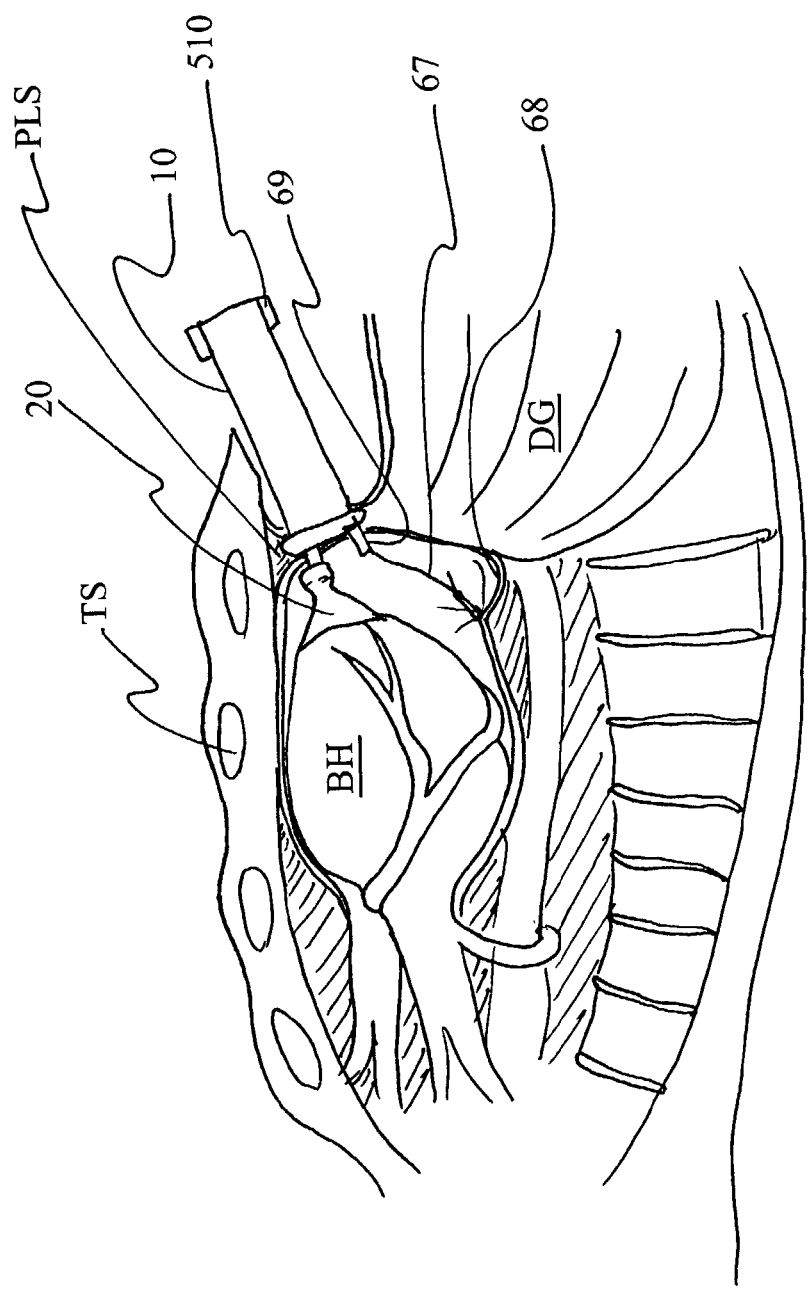
FIG. 12 is a lateral section view of the thorax illustrating the deployment of a pericardium retraction device according to an aspect of the present invention.

FIG. 12 illustrates a pericardium retraction device 69 may be engaged in a hollow passageway 120 of access cannula 10 through an internal joint 180. In order to assist in the positioning and orienting of a beating heart generally during posterior artery revascularization, a suture 67 may be placed through the incised pericardium tissue 68. A pericardium traction force may be applied to said suture through said device 69. This helps to lift and orient the heart within the thoracic cavity. The amount of protrusion of device 69 from the distal open end 115, along with the fine adjustment position and orientation of said device 69 within internal joint 180 will determine a vector direction in which the pericardium retraction load is applied to pericardium tissue by virtue of engaged suture 67. Said pericardium retraction device may be used singly or may assist the heart manipulator 20 in setting the desired position and orientation of a beating heart.

In broad terms, the surgical procedure for the set-up and deployment of the surgical apparatus during a beating heart CABG surgery, and relating to the present invention consists of:

1. Performing a single lung deflation, preferably on the left lung, in order to augment the pleural space PLS available for subsequent deployment of surgical apparatus within a closed chest;
2. Inserting one or more visioning ports into the thoracic cavity through intercostal port incisions (this step may be optional if such ports will only be deployed through an access lumen in access cannula 10);
3. Performing an abdominal incision (AI) preferably in the upper left quadrant of the patient;
4. Inserting a laparoscopic cannula 499 into the abdominal incision AI and directing it into the underlying extra-peritoneal space EPS, generally in a direction towards the patient's head;
5. Introducing $CO_2$ gas through a hollow laparoscopic cannula 499 to assist in the dissection of the extra-peritoneal space EPS and the lateral displacement of viceral organs (VO) contained within the peritoneum (PER);
6. Creating a sagittal tunnel spanning from the site of the abdominal incision AI to the patient's diaphragm DG, preferably in the vicinity of the left leaflet of the diaphragm;
7. Inserting a guide wire 400 through the center of laparoscopic cannula 499 in order to pierce diaphragm and obtain access into the thoracic cavity and more specifically the pleural space PLS;
8. Retrieving from the patient's body laparoscopic cannula 499, leaving behind guide wire 400 extending from the extracorporeal space, through the abdominal incision, along the sagittal tunnel, through the diaphragm, and into the pleural space;
9. Channeling a hollow enlarging cannula 402 (with conical tip) over guide wire 400 in order to reach the diaphragm and subsequently pierce through said diaphragm, preferably with a Seldinger technique, in order to obtain access into the pleural space;
10. Inserting diaphragm tissue retractor 40 over enlarging cannula 402 in order to further pierce diaphragm;
11. Retracting diaphragm tissue to obtain access into the thoracic cavity and more specifically into the pleural space;
12. Once the desired retracted opening in the diaphragm is obtained, inserting access cannula 10 through the center of diaphragm retractor 40 in a manner that the distal open end 115 of said cannula extends at least partially within and communicates with the pleural space;

13. Retrieving the diaphragm retractor 40 from the patient's body leaving in place access cannula 10 engaged with the retracted diaphragm at location of weir 130;
14. Deploying a visioning port into pleural space through an access lumen in access cannula 10 (optional if only intercostal port access will be used for vision system);
15. Introducing CO2 gas into the closed chest thoracic cavity of the patient either through an access lumen 125 in access cannula 10 or through an intercostal port incision, thereby augmenting the available pleural space through a displacement of the diaphragm caused by a pressure load acting on the dome of the diaphragm;
16. Alternatively, if CO2 is not introduced, applying a pulling load to access cannula 10 which will also displace diaphragm by virtue of its engagement with weir 130 thereby augmenting pleural space;
17. Positioning and orienting access cannula 10 relative to the patient's pleural space and target internal cardiac tissue contained therein;
18. Securing access cannula 10 in the desired position and orientation through its engagement with surgical arm 50;
19. Surgical harvesting of the internal mammary artery (IMA) if so required for a bypass graft. Deploying a forcep and cauterizing scalpel or a forcep and surgical scissor through the at least one hollow passageway 120 of access cannula 10 (FIG. 22A);
20. Incising the pericardium tissue of the beating heart, at least in the vicinity of the target coronary artery, to expose the myocardium prior to a distal anastomosis (for multi-vessel CABG cases incising the pericadium along the long axis of the heart preferably with an inverted T incision) (FIG. 22E);
21. Engaging a portion of the surface of the beating heart, preferably the apex, with a heart manipulator 20. (In single vessel CABG cases the heart manipulator 20 may be engaged with the pericardium tissue if the pericardiotomy incision was substantially small);
22. Deploying heart manipulator 20 in order to position and orient the beating heart within the thoracic cavity in a desired position and orientation for a surgical procedure;
23. Rotating access cannula 10 with respect to its centerline in order to select the optimum path for the deployment of coronary stabilizer 30 through access cannula 10, given the specific patient anatomy;
24. If desired, engaging the pericardium tissue, preferably the incised pericardium tissue, with a suture and applying a retraction load through pericardium retraction device 69 to assist in the positioning and orientation of the beating heart;
25. Deploying coronary stabilizer 30 through access cannula 10 while engaged in internal joint 180. Position and orient the heart contact member 301 through the numerous motion degrees of freedom offered in such a manner as to align the arterial window with the target coronary artery and the heart contact plane substantially tangent to the surface of the heart proximate to the target artery.
26. Compressing the heart surface gradually until pulsating effect of beating heart is substantially suppressed by virtue of the imposed immobilization load.
27. Securing the position and orientation of the coronary stabilizer through internal clamp 180, securing bolt 385, dial 371, and dial 331;
28. Entering a bypass vascular conduit into the pleural space either through a hollow passageway 120 or a designated access lumen 125 of access cannula 10. The vascular conduit may be kept engaged with a forceps 91 that is secured in a desired position and orientation relative the beating heart thereby facilitating the distal anastomosis.
29. Occluding the target coronary artery, at a location upstream and downstream of the grafting site, with two occluding wires 303 that are manipulated and placed into engagement with both the beating heart and pedestals 310 of the coronary stabilizer 30, by two forceps 91 deployed through access cannula 10;
30. Performing an arteriotomy incision through the arterial window 304 of the coronary stabilizer 30 with a surgical scissors 92 deployed through access cannula 10;
31. Performing a distal anastomosis through the arterial window 304 of coronary stabilizer 30 with two forceps 91 and one needle holder 93 deployed through access cannula 10;
32. Verifying graft patency of newly grafted conduit with an endoscopic ultrasonic Doppler 97 deployed through access cannula 10;
33. Performing a proximal anastomosis on the aorta, preferably the descending aorta, with an endoscopic surgical instrument capable of rapidly connecting a shape memory alloy stent to which a vascular conduit is affixed to said descending aorta;
34. Alternatively, performing a proximal anastomosis on the aorta by deploying an endoscopic side biting clamp, an endoscopic hole punch, an endoscopic forceps 91, and one endoscopic needle holder 93 through access cannula 10;
35. Verifying graft patency of newly grafted conduit with an endoscopic ultrasonic Doppler 97 deployed through access cannula 10;
36. Once the distal and proximal anastomosis is completed, disengaging coronary stabilizer 30 from the beating heart surface and retract from said surface;
37. In multi-vessel CABG surgeries, repeating procedure (steps 22-36) for other target coronary arteries arteries;
38. Once all diseased arteries have been revascularized, retrieving access cannula 10 from the patient's body;
39. Re-inflating deflated lung, and proceed to closing all surgical incisions through standard medical practice.

A variety of different coronary artery grafts may be performed with the surgical apparatus according to the present invention. These include: a venous conduit grafted proximally to the descending aorta and distally to a target coronary artery, a harvested internal mammary artery grafted distally to a target coronary artery, a venous conduit grafted proximally to the substantially non-harvested internal mammary artery and distally to a target coronary artery; a radial artery conduit grafted proximally to the descending aorta and distally to a target coronary artery;

In the preferred embodiments according to the present invention, access to the thoracic cavity was achieved by piercing at least a portion of the diaphragm. Alternatively, the concepts and principles of the present invention may also be applied to a thoraco-phrenic dissociation surgical approach, whereby access to the thoracic cavity is achieved through a tunnel or passage created between the diaphragm and the patient's ribcage without piercing or penetrating the diaphragm.

In the preferred embodiments according to the present invention, access to the diaphragm and subsequently the thoracic cavity was achieved via the extraperitoneal space. Alternatively, the concepts and principles of the present invention may also be applied to an intraperitoneal surgical approach, in which at least a portion of the patient's peritoneal membrane is pierced or penetrated prior to attaining the thoracic cavity beyond the diaphragm.

Those skilled in the art will appreciate that the anatomic routing selected to attain the thoracic cavity according to the present invention may vary without departing from the spirit of the invention. Also, the thoracic cavity may be attained simultaneously though the deployment of one or more access cannulae 10 according to the present invention. For instance, one access cannula may be deployed to access the left pleural space, and one may be deployed to access the right pleural space.

Some of the features and concepts of the surgical apparatus according to the present invention may also be used in cardiac surgery performed through an open chest approach, whereby the patient's thoracic structure is not left anatomically intact during the said cardiac procedure. For instance, open chest cardiac surgery performed through a sternotomy incision where the patient's sternum is incised the ribcage subsequently retracted, open chest cardiac surgery performed though an intercostal thoracotomy where two adjacent ribs are laterally spread apart, open chest cardiac surgery through an intercostal thoracotomy including a partial extraction of a portion of a rib, or other open chest cardiac surgeries performed through other like surgical incisions in order to access internal cardiac tissue. In these open chest cardiac surgeries, the patient's thoracic structure constitutes the anatomic barrier according to the present invention.

In the same spirit, some of the features and concepts of the surgical apparatus according to the present invention may also be used in cardiac surgery performed through an intercostal access port whereby the patient's thoracic structure is left anatomically intact (closed chest) during the said cardiac procedure. Here again the patient's thoracic structure constitutes the anatomic barrier according to the present invention.

A number of preferred embodiments have been described in detail and a number of alternatives have also been described. As changes in, or additions to, the above described embodiments may be made without departing from the nature, spirit or scope of the invention, the invention is not limited by or to those details, but only by the appended claims.

We claim:

1. A method for performing an intervention on a target anatomic structure of a patient body using an implement, said target anatomic structure including a biological tissue, said body defining an abdominal cavity and a thoracic cavity separated by a diaphragm, said thoracic cavity being at least in part protected by a ribcage and containing at least a portion of said target anatomic structure, said diaphragm being at least in part attached to said ribcage, said body also including a non-target anatomic structure, said method comprising the steps of:
    altering the configuration of said diaphragm to create a passageway leading into said thoracic cavity;
    introducing said implement at least partially into said thoracic cavity through said passageway in an implement operational configuration; and
    using said implement while the implement extends through said passageway to perform said intervention on said target anatomic structure, said intervention including performing a coronary artery bypass graft.

2. A method as recited in claim 1 wherein the step of altering the configuration of said diaphragm includes displacing said diaphragm.

3. A method as recited in claim 1 wherein the step of altering the configuration of said diaphragm includes dissociating at least partially said diaphragm from said ribcage.

4. A method as recited in claim 1 wherein said implement is positioned in said implement operational configuration through a thoraco-phrenic dissociation by inserting said implement between said ribcage and said diaphragm.

5. A method as recited in claim 1 wherein the step of altering the configuration of said diaphragm includes the step of traversing said diaphragm.

6. A method as recited in claim 1 wherein said implement is positioned in said implement operational configuration by inserting said implement through said diaphragm.

7. A method as recited in claim 1 further comprising the step of inserting said implement at least partially into said abdominal cavity prior to introducing said implement at least partially into said thoracic cavity through said diaphragm.

8. A method as recited in claim 1 wherein said intervention is performed at least partially while said implement extends at least partially into both said abdominal and thoracic cavities and through said diaphragm.

9. A method as recited in claim 1 wherein said implement is positioned so as to extend at least partially into the extra-peritoneal space of said abdominal cavity without penetrating into the peritoneal space of the abdominal cavity.

10. A method as recited in claim 1 wherein said intervention is performed at least partially while said implement extends from the exterior of said patient body, into said abdominal cavity, through said diaphragm and into said thoracic cavity.

11. A method as recited in claim 1 wherein said intervention includes the step of traversing across an external surface of said biological tissue.

12. A method as recited in claim 1 wherein said intervention includes the step of severing at least a portion of said biological tissue.

13. A method as recited in claim 1 wherein said intervention includes the step of puncturing at least a portion of said biological tissue.

14. A method as recited in claim 1 wherein said intervention includes the step of retracting at least a portion of said biological tissue.

15. A method as recited in claim 1 wherein said coronary artery bypass graft is performed on a beating heart.

16. A method as recited in claim 1 further including the steps of:
    selecting a separating component, said separating component having a component peripheral wall at least partially encompassing a component channel, said separating component being usable to at least partially separate said component channel from said non-target anatomic structure;
    introducing said separating component at least partially into said thoracic cavity through said passageway in a separating component operational configuration; and
    using said separating component for positioning said implement in said implement operational configuration.

17. A method as recited in claim 16 further comprising the step of at least temporarily coupling said separating component to said diaphragm.

18. A method as recited in claim 16 further comprising the step of at least temporarily coupling said separating component in a predetermined spatial relationship relative to said thoracic cavity.

19. A method as recited in claim 16 further comprising the step of at least temporarily coupling said implement to said separating component.

20. A method as recited in claim 16 wherein said separating component is inserted in an access aperture formed in said diaphragm, said access aperture being formed by using a piercing instrument to pierce a lead aperture in said diaphragm.

21. A method as recited in claim 16 wherein said separating component extends in the extra-peritoneal space of said abdominal cavity, without penetrating into the peritoneal space of the abdominal cavity.

22. A method as recited in claim 1 wherein said intervention is selected from the group consisting of stabilizing said target anatomic structure within said thoracic cavity and positioning said target anatomic structure within said thoracic cavity.

23. A method as recited in claim 1 wherein said intervention includes suctioning at least a portion of said target anatomic structure.

24. A method as recited in claim 1 wherein said intervention includes grasping at least a portion of said target anatomic structure.

25. A method as recited in claim 1 wherein said intervention includes abuttingly contacting at least a portion of said target anatomic structure.

26. A method as recited in claim 1 wherein said intervention includes harvesting of a vascular conduit for use in said revascularization procedure.

27. A method as recited in claim 1 wherein said intervention includes assessing blood flow through a vascular conduit of said target anatomic structure.

28. A method as recited in claim 1 wherein said intervention includes controlling blood flow through a vascular conduit of said target anatomic structure.

29. A method for performing an intervention on a target anatomic structure of a patient body using a first and a second implement, said target anatomic structure including a biological tissue, said body defining an abdominal cavity and a thoracic cavity separated by a diaphragm, said thoracic cavity being at least in part protected by a ribcage and containing at least a portion of said target anatomic structure, said diaphragm being at least in part attached to said ribcage, said body also including a non-target anatomic structure, said method comprising the steps of:

altering the configuration of said diaphragm to create a passageway leading into said thoracic cavity;

introducing both said first and second implements at least partially into said thoracic cavity through said passageway respectively in a first implement operational configuration and in a second implement operational configuration;

cooperatively using both said first and second implements while the first and second implements are respectively in said first and second implement operational configurations to perform said intervention on said target anatomic structure;

selecting a separating component, said separating component having a component peripheral wall at least partially encompassing a component channel, said separating component being usable to at least partially separate said component channel from said non-target anatomic structure;

introducing said separating component at least partially into said thoracic cavity through said passageway in a separating component operational configuration;

using said separating component for positioning said first and second implements respectively in said first and second implement operational configurations; and wherein one of said first or second implements is a beating heart stabilizer, said method further comprising the step of exerting a stabilizing force on a beating heart with said beating heart stabilizer.

30. A method as recited in claim 29 further comprising the steps of:

movably coupling said beating heart stabilizer to said separating component so as to allow a relative movement therebetween; and locking said beating heart stabilizer and said separating component in a predetermined spatial relationship relative to each other to maintain said stabilizing force on said beating heart, at least for part of said intervention.

31. A method as recited in claim 29 wherein one of said first or second implements is a heart manipulator, said method further comprising the step of positioning a heart with said heart manipulator within said thoracic cavity.

* * * * *